United States Patent [19]

Okada et al.

[11] Patent Number: 4,971,888
[45] Date of Patent: Nov. 20, 1990

[54] SILVER HALIDE PHOTOGRAPHIC MATERIAL

[75] Inventors: Hisashi Okada; Morio Yagihara; Kazunobu Katoh, all of Ashigara, Japan

[73] Assignee: Fuji Photo Film Co., Ltd., Ashigara, Japan

[21] Appl. No.: 349,170

[22] Filed: May 9, 1989

[30] Foreign Application Priority Data

May 11, 1988 [JP] Japan .................. 63-114119

[51] Int. Cl.⁵ .............................. G03C 1/06
[52] U.S. Cl. ............................ 430/264; 430/598
[58] Field of Search ....................... 430/264, 598

[56] References Cited

U.S. PATENT DOCUMENTS

| 4,798,780 | 1/1987 | Hall et al. | 430/264 |
| 4,824,764 | 4/1989 | Inagaki et al. | 430/264 |
| 4,847,180 | 7/1989 | Miyata et al. | 430/264 |

FOREIGN PATENT DOCUMENTS

| 0286062 | 10/1988 | European Pat. Off. | 430/598 |
| 0286840 | 10/1988 | European Pat. Off. | 430/598 |

Primary Examiner—Paul R. Michl
Assistant Examiner—Janet C. Baxter
Attorney, Agent, or Firm—Burns, Doane, Swecker & Mathis

[57] ABSTRACT

A silver halide photographic material is disclosed, comprising a support having thereon at least one of silver halide photographic emulsion layers and other hydrophilic colloidal layers, wherein said at least one of photographic emulsion layers and other hydrophobic colloidal layers contains a compound represented by formula (I)

$$X-N(A_1)-N(A_2)-G-R \quad (I)$$

wherein at least one of $A_1$ and $A_2$ represents a hydrogen atom and other represents a hydrogen atom, a sulfinic residual group or

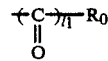

wherein $R_0$ represents an alkyl group, an alkenyl group, an aryl grup, an alkoxy group or an aryloxy group, and $l_1$ represents an integer of 1 or 2; G represents

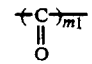

wherein $m_1$ represents an integer of 1 or 2, a sulfonyl group, a sulfoxy group

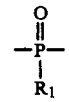

wherein $R_1$ represents an alkoxy grup or an aryloxy group, a thiocarbonyl grup or an iminomethylene group; X represents an aliphatic group, an aromatic group or a heterocyclic group, substituted by the group represented by formula (a):

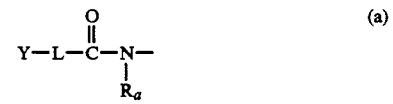

wherein Y represents a hydrogen atom, an aliphatic group, an aromatic group or a heterocyclic group; L represents

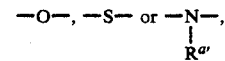

wherein $R_a'$ represents a hydrogen atom, an aliphatic group or an aromatic group; $R_a$ represents a hydrogen atom, an aliphatic group or an aromatic group; and R represents a group represented by formula (b):

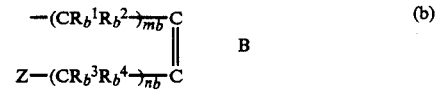

wherein $R_b^1$ to $R_b^4$ may be the same or different and each represents a hydrogen atom, an aliphatic group or an atomatic group; B represents a suitable atomic group for forming a 5- or 6-membered ring; Z represents a group capable of making a nucleophilic attach on G to separate the —G—R portion from the other portion of the formula; $m_b$ represents an integer of 0 or 1; $n_b$ represents an integer of 1 when Z is a hydroxy group, or $n_b$ represents an integer of 0 or 1 when Z represents a group other than a hydroxy group; and $(m_b+n_b)$ represents an integer of 1 or 2.

11 Claims, No Drawings

SILVER HALIDE PHOTOGRAPHIC MATERIAL

FIELD OF THE INVENTION

The present invention relates to a silver halide photographic material which provides a negative image having extremely high contrast, high sensitivity and excellent halftone quality, and a silver halide photographic material which provides a direct positive photographic image. More particularly, the present invention relates to a photographic light-sensitive material which includes a novel silver halide nucleating agent.

BACKGROUND OF THE INVENTION

U.S. Pat. No. 3,730,727 (developing solutions comprising a combination of ascorbic acid and hydrazine), U.S. Pat. No. 3,227,552 (use of hydrazine as an auxiliary developing agent for providing a direct positive color image), U.S. Pat. No. 3,386,831 (use of $\beta$-monophenylhydrazide of aliphatic carboxylic acid as a stabilizer for silver halide light-sensitive materials), U.S. Pat. No. 2,419,975, and Mees, *The Theory of Photographic Process*, 3rd Ed., 1966, page 281, disclose the use of hydrazine compounds in a silver halide photographic emulsions or developing solutions.

In particular, it is disclosed in U.S. Pat. No. 2,419,975 that a high contrast negative image can be obtained by the incorporation of a hydrazine compound.

The patent discloses that when a light-sensitive material comprising a silver bromochloride emulsion containing a hydrazine compound incorporated therein is developed with a developing solution having a high pH value such as 12.8, an extremely high contrast having a gamma value of more than 10 can be provided. However, strongly alkaline developing solutions having pH values of near 13 are susceptible to air oxidation and are unstable, they are, therefore, unsuitable for prolonged use or storage.

An ultrahigh contrast wherein a gamma value is more than 10 is extremely useful for the photographic reproduction of continuous tone images or the reproduction of line images by dot image processing which is useful for photoengraving regardless of whether negative images or positive images are formed. For this purpose, a light-sensitive material comprising a silver bromochloride photographic emulsion having a silver chloride content of 50 mol% or more and preferably 75 mol% or more, has been developed with a hydroquinone developing solution having an extremely low effective concentration of sulfinic ion (normally 0.1 mol/liter or less). However, because of its low sulfinic ion concentration, such a developing solution is extremely unstable and defies prolonged storage (e.g., more than 3 days).

Furthermore, these methods require the use of a silver bromochloride emulsion having a rather high silver chloride content and thus cannot provide high sensitivity. It has, therefore, been desired to obtain ultrahigh contrast useful for reproduction of dot images or line images using a high sensitivity emulsion and a stable developing solution.

The inventors have disclosed a silver halide photographic emulsion which is developed with a stable developing solution to provide an extremely high contrast (see U.S. Pat. Nos. 4,224,401, 4,168,977, 4,243,739, 4,272,614 and 4,323,643). However, it has been found that the acyl hydrazine compounds used in these emulsions have some disadvantages.

For example, the hydrazines have been known to produce nitrogen gas during development. The nitrogen gas forms bubbles in the film which damage photographic images. Furthermore, the nitrogen gas flows into the developing solution, adversely effecting other photographic light-sensitive materials.

In order to prevent nitrogen gas from flowing into the developing solution, a nucleating agent has been used which has a higher molecular weight which gives nondiffusibility. However, such a nondiffusible nucleating agent has been found to have unsuitable stability. In particular, upon aging a coating solution containing such a nucleating agent produces a precipitate which deteriorates the filterability thereof and even the photographic properties thereof.

Furthermore, these hydrazines are disadvantageous in that they need to be used in large amounts to provide sensitization and higher contrast. These hydrazines are also disadvantageous in that when they are used in combination with other sensitizing techniques (e.g., to increase chemical sensitization, increase grain size, sensitization accelerating compounds as described in U.S. Pat. Nos. 4,272,606 and 4,241,164 may be added) to render the light-sensitive material more sensitive, sensitization and/or fogging may occur during the storage of the light-sensitive material.

Therefore, it would be beneficial to provide a compound which can reduce bubble production and the flow of bubbles into the developing solution, which causes no stability problems with time, and can be used in extremely small amounts to provide high contrast.

U.S. Pat. Nos. 4,385,108, 4,269,929 and 4,243,739 indicate that hydrazines containing substituents which are easily adsorbed by silver halide grains can be used to obtain extremely high contrast negative gradation. Among hydrazine compounds containing such adsorption groups, the specific examples described above are disadvantageous in that they are subject to desensitization with time upon storage.

On the other hand, there are various direct positive photographic processes. Among these processes, the most useful are processes in which silver halide grains are exposed to light in the presence of a desensitizer and then developed, and processes in which silver halide emulsions containing light-sensitive nuclei primarily within the silver halide grains are exposed to light and then developed in the presence of a nucleating agent. The present invention relates to the latter type of process. A silver halide emulsion containing light-sensitive nuclei primarily within the silver halide grains which forms latent images therein is commonly referred to as an internal latent image-type silver halide emulsion. This type of emulsion is distinguished from silver halide emulsions which form latent images primarily on the surface of silver halide grains.

There are known processes in which internal latent image-type silver halide photographic emulsions are surface-developed in the presence of a nucleating agent to provide direct positive images, as well as photographic emulsions or light-sensitive materials for use in such processes.

In the above described processes for the formation of direct positive images, nucleating agents have been incorporated in the developing solution. Also, nucleating agents have been incorporated in the photographic emulsion layer or other proper layers in light-sensitive materials so that when it is adsorbed by the surface of silver halide grains, better reversal properties can be obtained.

Examples of such nucleating agents include hydrazines such as those described in U.S. Pat. Nos. 2,563,785 and 2,588,982, hydrazide and hydrazine compounds such as those described in U.S. Pat. No. 3,227,552, heterocyclic quaternary salt compounds such as those described in U.S. Pat. Nos. 3,615,615, 3,719,494, 3,734,738, 4,094,683 and 4,115,122, British Pat. No. 1,283,835, and JP-A-52-3426 and JP-A-52-69613 (the term "JP-A" as used herein refers to a "published unexamined Japanese patent application"), thiourea-bound acylphenylhydrazine compounds such as those described in U.S. Pat. Nos. 4,030,925, 4,031,127, 4,139,387, 4,245,037, 4,255,511 and 4,276,364 and British Pat. No. 2,012,443, compounds containing as adsorption groups heterocyclic thioamide such as those described in U.S. Pat. No. 4,080,207, phenylacylhydrazine compounds containing heterocyclic groups comprising mercapto groups as adsorption groups such as those described in British Pat. No. 2,011,397B, sensitizing dyes containing in the molecular structure thereof substituents having a nucleating effect such as those described in U.S. Pat. No. 3,718,470, and hydrazine compounds such as those described in JP-A-59-200230, JP-A-59-212828 and JP-A-59212829 and *Research Disclosure*, No. 23510 (January, 1953).

However, these compounds have been found disadvantageous in that they provide insufficient activity as nucleating agents. Even when they provide sufficient activity, their preservability has been found to be insufficient. Their activity may be deteriorated by the time when it is coated on a support in the form of an emulsion. If they are used in large amounts, they deteriorate the properties of the prepared film.

In order to overcome these disadvantages, some compounds have been proposed such as the adsorption-type hydrazine derivatives described in JP-A-60-179734, JP-A-61-170733, JP-A-62-65034, JP-A-61-270744 and JP-A-62-948, and the hydrazine derivatives containing modified groups described in JP-A-62-270948 and JP-A-63-29751. However, none of these compounds have exhibited sufficient nucleation activity to meet the demands for improving stability of the developing solution (i.e., preventing deterioration of the developing agent) by lowering the pH value of the processing solution, shortening processing time, and/or reducing the dependence of the change in the composition of the developing solution (e.g., pH, sodium sulfite).

SUMMARY OF THE INVENTION

Accordingly, it is an object of the present invention to provide a silver halide photographic material which can provide an extremely high contrast negative gradation having a gamma value of more than 10 using a stable developing solution.

It is another object of the present invention to provide a negative-type silver halide photographic material containing high activity hydrazines which can be used in small amounts to provide a high contrast negative gradation using a low pH developing solution without adversely effecting photographic properties.

It is further object of the present invention to provide a direct positive-type silver halide photographic material containing high activity hydrazines which can provide excellent reversal properties using a low pH developing solution.

It is still further object of the present invention to provide a silver halide photographic material with excellent aging stability containing hydrazines which can be easily synthesized and have excellent preservability.

It is additional object of the present invention to provide a silver halide photographic material containing an emulsion having excellent aging stability and which varies little in activity during preparation.

The above objects of the present invention may be accomplished with a silver halide photographic material comprising a support having thereon at least one of silver halide photographic emulsion layers and other hydrophilic colloidal layers, wherein said at least one of photographic emulsion layers and other hydrophilic colloidal layers contains a compound represented by formula (I)

wherein at least one of $A_1$ and $A_2$ represents a hydrogen atom or the other represents a hydrogen atom, a sulfinic residual group or

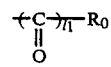

in which $R_0$ represents an alkyl group, an alkenyl group, an aryl group, an alkoxy group or an aryloxy group, and $l_1$ represents an integer of 1 or 2; G represents

in which $m_l$ represents an integer of 1 or 2, a sulfonyl group, a sulfoxy group,

in which $R_1$ represents an alkoxy group or an aryloxy group, a thiocarbonyl group or an iminomethylene group; X represents an aliphatic group, an aromatic group or a heterocyclic group, substituted by the group represented by formula (a):

wherein Y represents a hydrogen atom, an aliphatic group, an aromatic group or a heterocyclic group; L represents

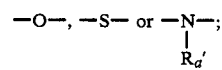

$R_a$ and $R_2'$ each represents a hydrogen atom, an aliphatic group or an aromatic group; and R represents a group represented by formula (b):

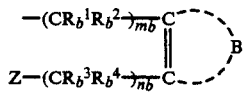

wherein $R_4^1$ and $R_b^4$ may be the same or different and each represents a hydrogen atom, an aliphatic group or an aromatic group; B represents a suitable atomic group for forming a 5- or 6-membered ring; Z represents a group capable of making a nucleophilic attack on G to separate the —G—R portion from the other portion of the formula; $m_b$ represents an integer of 0 or 1; $n_b$ represents an integer of 1 when Z is a hydroxy group or $n_b$ represents an integer of 0 or 1 when Z represents a group other than a hydroxy group; and $(m_b+n_b)$ represents an integer of 1 or 2.

DETAILED DESCRIPTION OF THE INVENTION

In formula (I), $A_1$ and $A_2$ each represents a hydrogen atom, an alkylsulfonyl group or an arylsulfonyl group having 20 or less carbon atoms and preferably a phenylsulfonyl group or a substituted phenylsulfonyl group so substituted that the sum of hammett's substituent constants is —0.5 or more, or

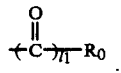

in which $R_0$ preferably represents a straight chain, branched or cyclic alkyl group, an alkenyl group, an aryl group and preferably a phenyl group or a substituted phenyl group so substituted that the sum of Hammett's substituent constants is —0.5 or more, an alkoxy group such as an ethoxy group, or an aryloxy group and preferably a monocyclic aryloxy group such as a phenyl group. The alkyl group, alkenyl group, aryl group, alkoxy group or aryloxy group preferably have 30 or less carbon atoms and may be substituted. Examples of such substituents include alkyl groups, aralkyl groups, alkenyl groups, alkynyl groups, alkoxy groups, aryl groups, substituted amino groups, acylamino groups, sulfonylamino groups, ureido groups, urethane groups, aryloxy groups, sulfamoyl groups, carbamoyl groups, alkylthio groups, arylthio groups, sulfonyl groups, sulfinyl groups, hydroxy groups, halogen atoms, cyano groups, sulfo groups, carboxyl groups, alkyl or aryloxycarbonyl groups, acyl groups, alkoxycarbonyl groups, acyloxy groups, carbonamide groups, sulfonamide groups, nitro groups, alkylthio groups and arylthio groups. Specific examples of sulfinic acid residual groups represented by $A_1$ or $A_2$ are described in U.S. Pat. No. 4,478,928. Preferably $A_1$ and $A_2$ are both hydrogen atoms.

In formula (I), preferred among those groups represented by G is

In formula (I), the aliphatic group represented by X is a straight chain, branched or cyclic alkyl group, alkenyl group or alkynyl group, and preferably has from 1 to 30 carbon atoms.

If X is an aromatic group, it is preferred to be a monocyclic or bicyclic aryl group such as a phenyl group or a naphthyl group, particularly having from 6 to 30 carbon atoms.

If X is a heterocyclic group, it is preferably a 3-membered to 10-membered saturated or unsaturated heterocyclic group containing at least one of a nitrogen atom, an oxygen atom and a sulfur atom. Such a heterocyclic group may be a monocyclic group or may form a condensed ring with other aromatic groups or heterocyclic groups. More preferably, the heterocyclic group is a 5-membered or 6-membered aromatic heterocyclic group containing, e.g., a pyridine group, an imidazolyl group, a quinolinyl group, a benzimidazolyl group, a pyrimidyl group, a pyrazolyl group, an isoquinolinyl group, a thiazolyl group or a benzothiazolyl group.

Even more preferred among the groups represented by X are aromatic groups, nitrogen-containing heterocyclic groups and groups represented by formula (c):

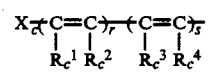

wherein $X_c$ represents an aromatic group or a nitrogen-containing heterocyclic group, preferably having from 6 to 30 carbon atoms; $R_1^1$ to $R_c^4$ each represents a hydrogen atom, a halogen atom or an alkyl group; optionally $X_c$ and $R_c^1$ to $R_c^4$ may be substituted; and r and s each represents the integers of 0 or 1.

Most preferably, X represents an aromatic group, particularly an aryl group having from 6 to 30 carbon atoms.

X may be substituted. Besides the substituents represented by formula (a), X may be substituted with groups such as alkyl groups, aralkyl groups, alkenyl groups, alkynyl groups, alkoxy groups, aryl groups, substituted amino groups, acylamino groups, sulfonylamino groups, ureido groups, urethane groups, aryloxy groups, sulfamoyl groups, carbamoyl groups, alkylthio groups, arylthio groups, sulfonyl groups, sulfinyl groups, hydroxy groups, halogen atoms, cyano groups, sulfo groups, carboxyl groups, alkyl groups, aryloxycarbonyl groups, acyl groups, alkoxycarbonyl groups, acyloxy groups, carbonamide groups, sulfonamide groups, nitro groups, alkylthio groups, and arylthio groups. These groups may also be further substituted. In addition, they may be connected to each other to form a ring.

X may contain one or more groups represented by formula (a).

In formula (a), L preferably represents —O—, —S— or —NH—.

In formula (a), the aliphatic group represented by Y is a straight chain, branched or cyclic alkyl group, alkenyl group or alkynyl group, and preferably has from 1 to 30 carbon atoms.

If Y is an aromatic group, it is preferably a monocyclic or bicyclic aryl group such as a phenyl group or a naphthyl group, particularly having from 6 to 30 carbon atoms.

If Y is a heterocyclic group, it is preferably a 3-membered to 10-membered saturated or unsaturated heterocyclic group containing at least one of a nitrogen atom, an oxygen atom and a sulfur atom. Such a heterocyclic group may be a monocyclic group or may form a condensed ring with other aromatic groups or heterocyclic groups. More preferably, the heterocyclic group is a 5-membered or 6-membered aromatic heterocyclic group containing, e.g., a pyridine group, an imidazolyl group, a quinolinyl group, a benzimidazolyl group, a pyrimidyl group, a pyrazolyl group, an isoquinolinyl group, a thiazolyl group or a benzothiazolyl group.

Y may be substituted with, for example, alkyl groups, aralkyl groups, alkenyl groups, alkynyl groups, alkoxy groups, aryl groups, substituted amino groups, acylamino groups, sulfonylamino groups, ureido groups, urethane groups, aryloxy groups, sulfamoyl groups, carbamoyl groups, alkylthio groups, arylthio groups, sulfonyl groups, sulfinyl groups, hydroxy groups, halogen atoms, cyano groups, sulfo groups, carboxyl groups, alkyloxycarbonyl groups, aryloxycarbonyl groups, acyl groups, alkoxycarbonyl groups, acyloxy groups, carbonamide groups, sulfonamide groups, nitro groups, alkylthio groups and arylthio groups. These groups may also be further substituted.

In addition, the groups may be connected to each other to form a ring.

In formula (a), if either $R_a$ or $R_a'$ is an aliphatic group (when L is represented by

it is preferably a straight chain, branched or cyclic alkyl group, alkenyl group or alkynyl group, particularly having 1 to 20 carbon atoms.

The aromatic groups represented by $R_a$ and $R_a'$ are preferably monocyclic or bicyclic aryl groups such as phenyl groups, particularly having from 6 to 20 carbon atoms.

$R_a$ and $R_a'$ may also be substituted with, for example, those substituents described with reference to Y in formula (a). Optionally, Y and $R_a$, Y and $R_a'$, and $R_a$ and $R_a'$ may be connected to each other to form a ring. Most preferably, $R_a$ and $R_a'$ are hydrogen atoms.

In formula (b), $R_b^1$ to $R_b^4$ may be the same or different and each represents a hydrogen atom, an aliphatic group (preferably having from 1 to 12 carbon atoms) such as straight chain, branched or cyclic alkyl groups, alkenyl groups or alkynyl groups, or an aromatic group (preferably having from 6 to 12 carbon atoms) such as monocyclic or bicyclic aryl groups (e.g., a phenyl group or a naphthyl group).

Each of $R_b^1$ to $R_b^4$ is more preferably a hydrogen atom.

In formula (b), B represents an atomic group required to form a 5-membered or 6-membered ring, which may be substituted. Suitable substituents include those described with reference to Y in formula (a). Examples of the 5-membered or 6-membered rings represented by B include aliphatic groups such as a cyclohexene ring, aromatic groups such as a benzene ring and naphthalene ring, and heterocyclic groups such as a pyridine ring and quinoline ring. Preferred among these groups is an aromatic group. Particularly preferred among these groups is the benzene ring.

In formula (b), Z represents a group which can make a nucleophilic attack on G in the following reaction intermediate produced by oxidation or reaction of a hydrazine compound of formula (I) to separate X—N=N group from G.

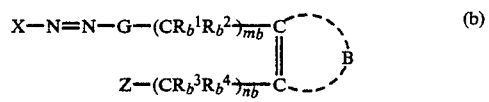

Particularly, Z may be a functional group which directly reacts with G, such as OH, SH or $NHR_z$ in which $R_z$ represents a hydrogen atom, an alkyl group, an aryl group, a heterocyclic group,

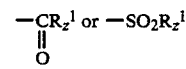

wherein $R_z^1$ represents a hydrogen atom, an alkyl group, an aryl group or a heterocyclic group (OH, SH and $NHR_z$ may be temporarily protected by, e.g., hydrolysis of alkali which produces these groups), or a functional group which reacts with a nucleophilic agent such as a hydroxyl ion or a sulfinic acid ion to become capable of reacting with G, such as

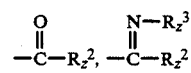

in which $R_z^2$ and $R_z^3$ each represents a hydrogen atom, an alkyl group, an alkynyl group, an aryl group, or a heterocyclic group.

In formula (b), $m_b$ represents an integer of 0 or 1; $n_b$ represents an integer of 1 when Z represents a hydroxy group or an integer of 0 or 1 when Z represents a group other than a hydroxy group; and $m_b$ and $n_b$ (i.e., $m_b+n_b$) satisfy the equation $(m_b+n_b)=1$ or 2.

In formula (I), preferred among the structures represented by —G—R is one represented by the formula (d):

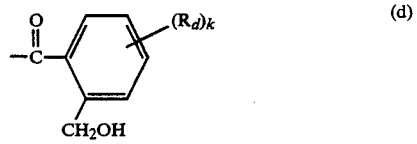

wherein $R_d$ has the same meaning as those described as substituents for X in formula (I); and k represents an integer of 0, 1 or 2. When k is 2, the two $R_d$ groups may be the same or different.

X or R in formula (I) may contain a ballast group commonly used in an immobile photographic additive such as a coupler. A ballast group is an organic group which provides sufficient molecular weight to prevent the compound of formula (I) from substantially diffusing into other layers or a processing solution. Such a ballast group contains a combination of one or more of an alkyl group, an aryl group, a heterocyclic group, an ether group, a thioether group, an amide group, a ureido group, a urethane group, a sulfonamide group, etc. As such a ballast group there may be preferably used one containing a substituted benzene ring and particularly preferably one containing a benzene ring substituted by branched alkyl group.

Particularly preferred among compounds represented by formula (I) is one represented by formula (II):

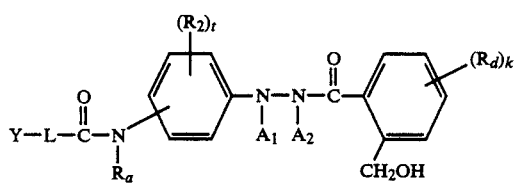

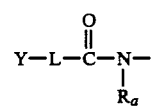

wherein L, Y, $R_a$, $A_1$, $A_2$, $R_d$ and k have the same meaning as those defined in formulae (I), (a) and (d); $R_2$ has the same meaning as the substituents for Y in formula (a); and t represents an integer 0, 1 or 2, with the proviso that when t is 2, the two $R_2$ groups may be the same or different.

More preferably, the group is substituted at the ortho position or para position of the hydrazino group.

Specific examples of the compound represented by formula (I) will be shown hereinafter, but the present invention should not be construed as being limited thereto.

1.

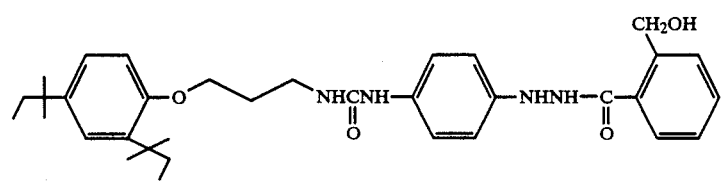

2.

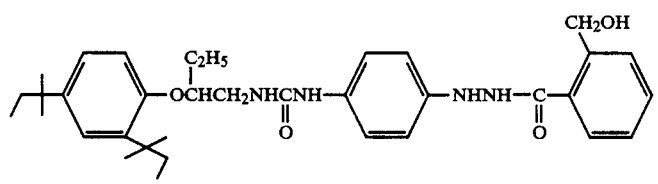

3.

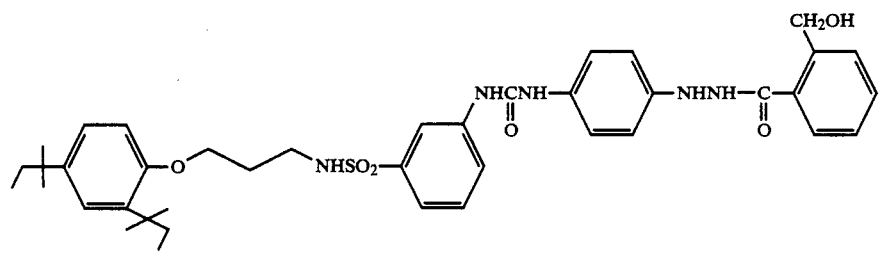

4.

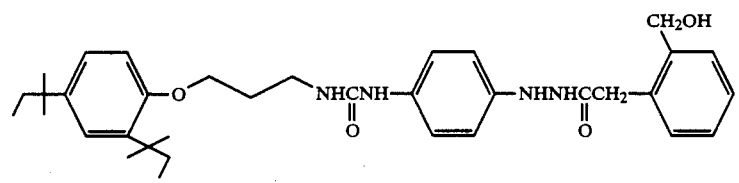

5.

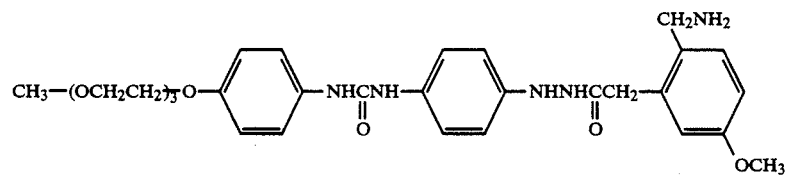

6.

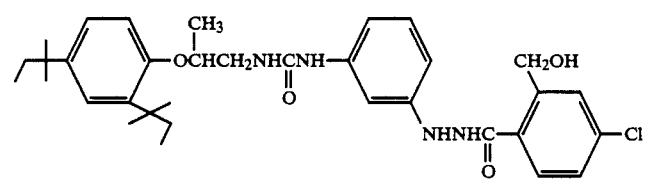

7.
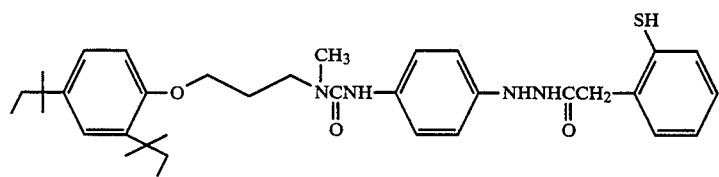
8.
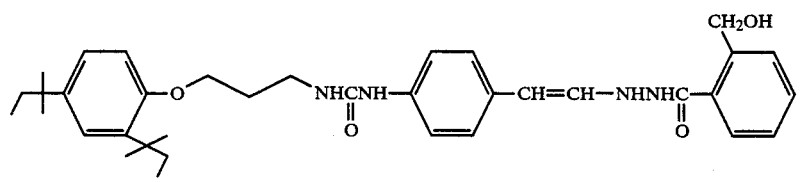
9.
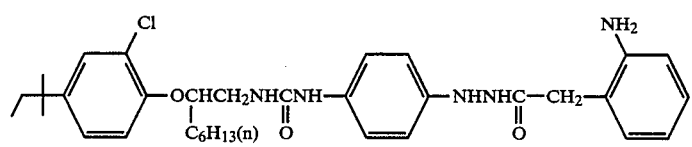
10.
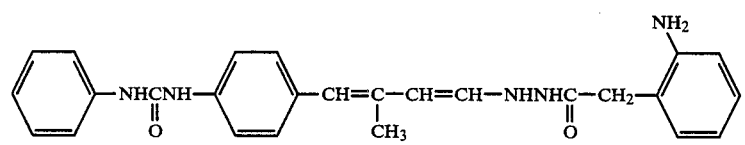
11.
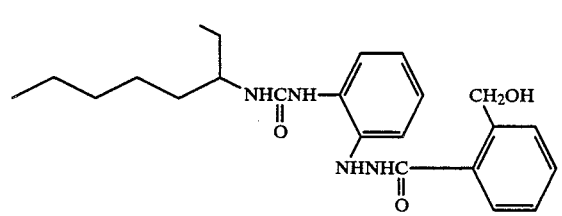
12.
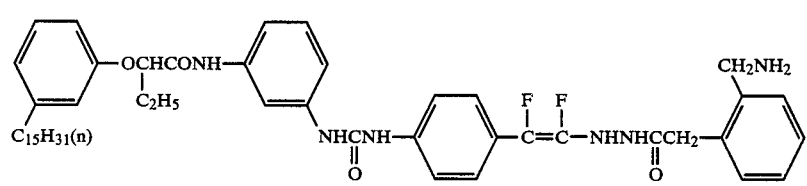
13.
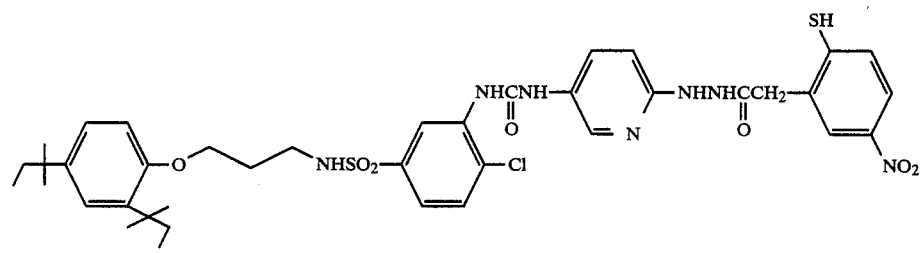
14.
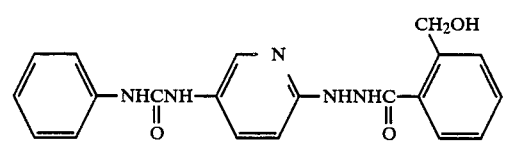

15.
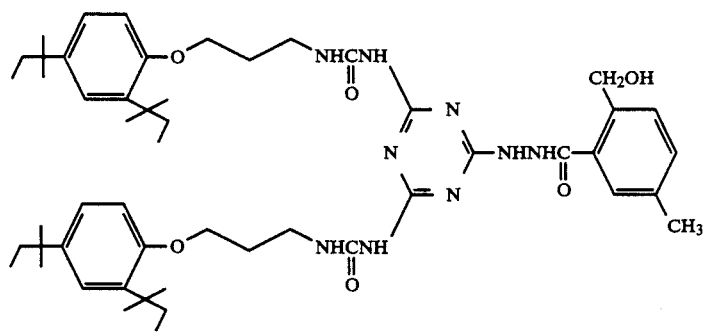
16.
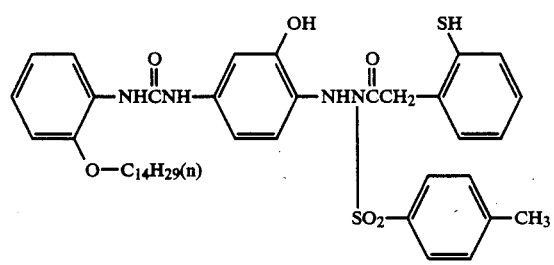
17.
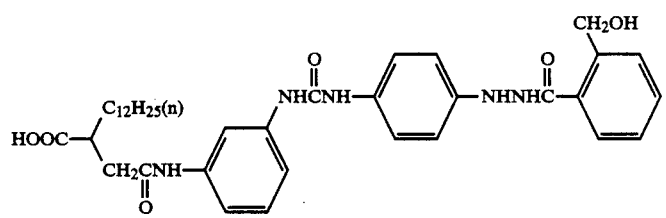
18.
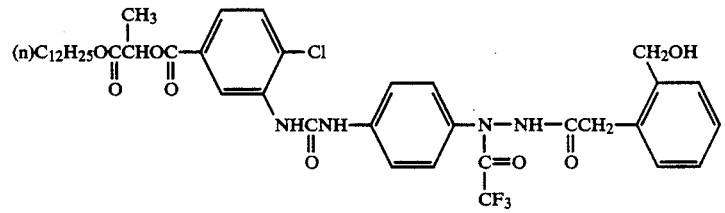
19.
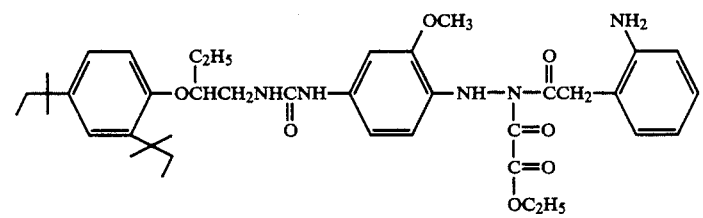
20.
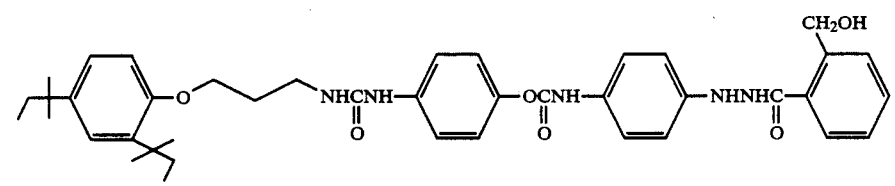
21.
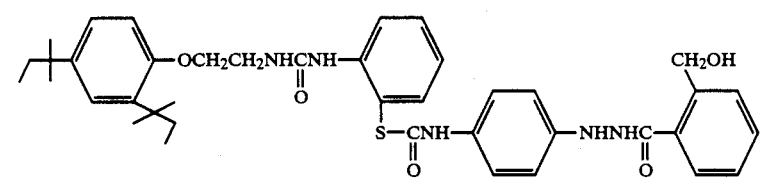

-continued
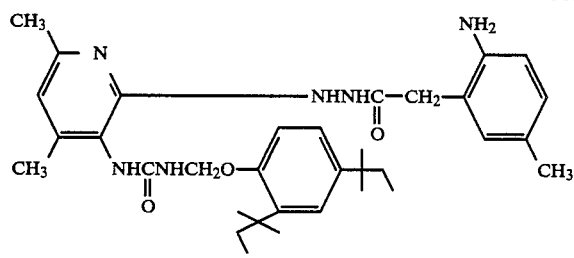 22.
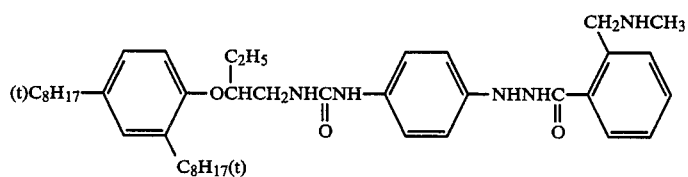 23.
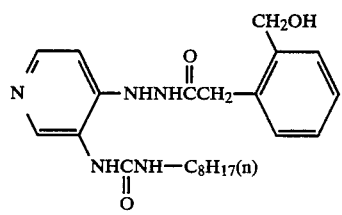 24.
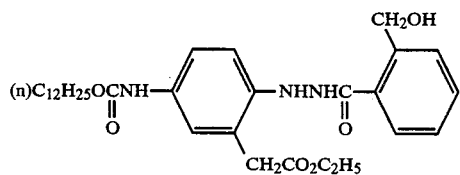 25.
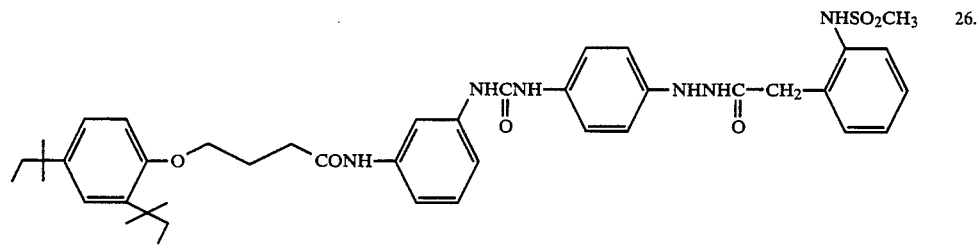 26.
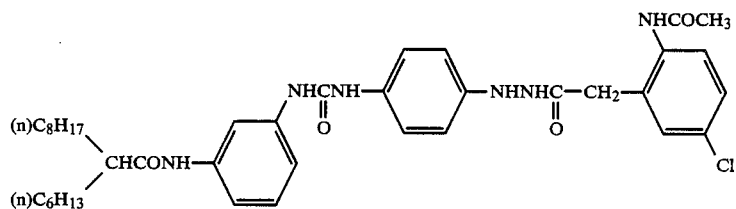 27.
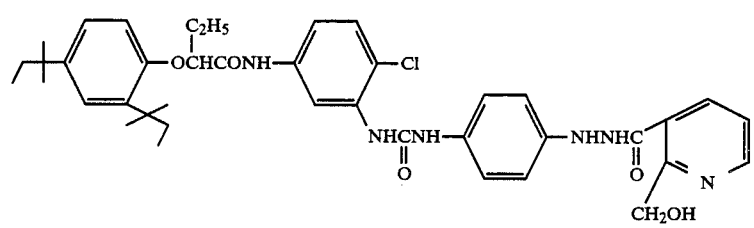 28.

-continued

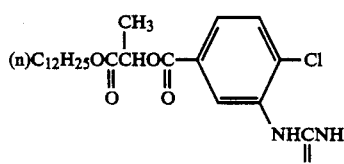
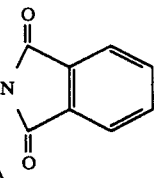

29.

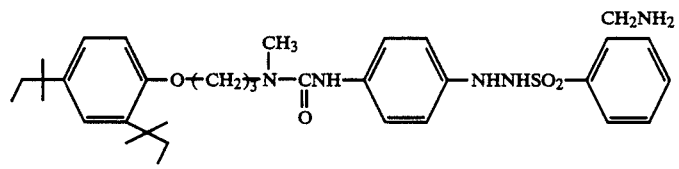

30.

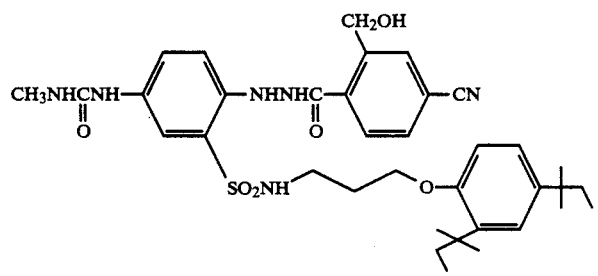

31.

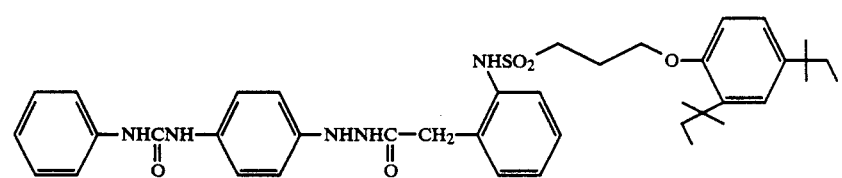

32.

In the above compounds represented by formula (I),

" /⊦ " represents "CH$_3$—CH$_2$—C(CH$_3$)(CH$_3$)— ".

" ⁀⁀⁀ " represents "—CH$_2$—CH$_2$—CH$_2$—".

" ⋀⋁⋀ " represents " CH$_3$—CH$_2$—CH$_2$—CH$_2$—CH$_2$\\CH— / CH$_3$—CH$_2$ ".

The synthesis of compounds represented by formula (I) will be described by way of example below.

SYNTHESIS EXAMPLE 1

Synthesis of Compound 1

41.3 g of 4-nitrophenylhydrazine and 33 g of phthalide were dissolved in 300 ml of acetonitrile. The solution was heated under reflux with stirring over 4 hours. The reaction solution was allowed to stand for cooling to room temperature. The resulting solid was then filtered off, and recrystallized from acetonitrile to obtain 15.1 g of 1-(2'-hydroxymethylbenzoyl)-2-(4-nitrophenyl)hydrazine (yield of 21.0%).

9.1 g of the nitro compound as obtained above was dissolved in 210 ml of ethanol and 90 ml of water in an atmosphere of nitrogen. A solution of 27 g of hydrosulfite in 120 ml of water was dropwise added to the solution. The mixture was then stirred at room temperature over 30 minutes. The mixture was further stirred at a temperature of 60° C. over 15 minutes. The insoluble matter was then filtered off. The filtrate was concentrated under reduced pressure. 100 ml of water was added to the solution. The resulting crystal was filtered off, and then recrystallized from ethanol. 6.30 g (77.2% yield of 2-(4-aminophenyl)-1-(2,-hydroxymethylbenzoyl)hydrazine was obtained.

2.57 g of the above amino compound was dissolved in 25 ml of N,N-dimethylacetamide in an atmosphere of nitrogen. The solution was cooled to a temperature of 0° C. or lower. 1.21 ml of N-methylmorpholine was added to the solution. 1.26 ml of phenyl chloroformate was then dropwise added to the solution. During this dropwise addition, the solution was cooled with stirring so that the temperature thereof did not exceed 0° C. The solution was further stirred at a temperature of 0° C. or less for 1 hour. 2.93 ml of triethylamine was added to the solution. A solution of 2.91 g of 3-(2,4-di-tert-pentylphenoxy)-1-propylamine in 10 ml of acetonitrile was dropwise added to the solution. After being heated to a temperature of 50° C. with stirring over 1 hour, the solution was then cooled to room temperature. The solution was then extracted with a mixture of 100 ml of ethyl acetate and 100 ml of dilute hydrochloric acid (0.5 mol/liter). The resulting organic phase was washed with saturated brine, dried with anhydrous sodium sulfate, filtered off, and then concentrated. The concentrated filtrate was then subjected to separation and purification through a silica gel column chromatography (developing solvent: 1/9 mixture (by volume) of methanol and chloroform). The crystal was then recrystallized from acetonitrile to obtain 3.04 g (53.0% yield) of Compound 1.

SYNTHESIS EXAMPLE 2

Synthesis of Compound 9

4.70 g of 4-[2-(2-chloro-4-pentylphenoxy)octaneureido]phenylhydrazine and 1.53 ml of triethylamine were dissolved in 50 ml of acetonitrile. The solution was cooled to 0° C. or below. 2.00 g of 2-nitrophenylacetyl chloride was dropwise added to the solution. During this dropwise addition, the solution was cooled with stirring so that the temperature thereof did not exceed 0° C. The solution was further stirred at a temperature of 0° C. for 2 hours. The solution was then poured into iced water. The solution was then extracted with ethyl acetate. The resulting organic phase was washed with saturated brine, dried with anhydrous sodium sulfate, filtered off, and then concentrated. The concentrated filtrate was then subjected to separation and purification through a silica gel column chromatography (developing solvent: 1/9 mixture (by volume) of methanol and chloroform) to obtain 2.62 g of 2-[4-(2-chloro-4-pentylphenoxy)octaneureido]phenyl-1-(2,-nitrophenylacetyl)-hydrazine (41.4% yield).

2.62 g of the above nitro compound was dissolved in 25 ml of methanol. The solution was then hydrogenated (10% Pd/c, $H_2$ 100 psi). The catalyst was removed from the solution. Methanol was then distilled off. The resulting crude product was subjected to separation and purification through a silica gel column chromatography (developing solvent: 1/9 mixture (by volume) of methanol and chloroform) to obtain 1.37 g (55.2% yield) of Compound 9.

The incorporation of the present compound in the photographic emulsion layer or hydrophilic colloid layer (particularly preferably in the photographic emulsion layer) can be accomplished by dissolving the compound in water or an organic solvent miscible with water (optionally adding alkali hydroxide or a tertiary amine to the solution to make a salt which will be then dissolved in the solution), and then adding the solution to a hydrophilic colloid solution (e.g., aqueous solution of silver halide or gelatin) while the pH value thereof may be optionally adjusted with an acid or alkali.

The compounds of the present invention may be used singly or in combination. The amount of the present compound to be incorporated is preferably in the range of from $1 \times 10^{-5}$ to $5 \times 10^{-2}$ mol and particularly preferably from $2 \times 10^{-5}$ to $1 \times 10^{-2}$ mol, per mol of silver halide, and can be properly selected depending on the properties of the silver halide emulsion to be used in combination.

The compound represented by formula (I) can be used in combination with a negative type emulsion to form a negative image with a high contrast. The compound may be also used in combination with an internal latent image type silver halide emulsion. The compound may be preferably used in combination with a negative-type emulsion to form a negative image with high contrast.

The average particle size of silver halide to be used in the formation of a negative image with a high contrast is preferably in the range of 0.7 $\mu$m or less (finely divided particle range) and particularly preferably 0.5 $\mu$m or less. The particle size distribution is not particularly limited but is preferably in the range of monodispersion. The term "monodispersion" as used herein means a particle composition such that at least 95% by weight or number of the total particles have a particle size within $\pm 40\%$ of the average particle size.

The silver halide grains to be incorporated in the photographic emulsion may have a regular crystal structure such as cubic, octahedron, rhombic dodecahedron, and tetradecahedron, an irregular crystal structure such as sphere and tabular, or a composite thereof.

The silver halide grains may have a structure such that the phase is uniform from the internal portion to the surface or different from the internal portion to the surface.

The silver halide emulsion to be used in the present invention may coexist cadmium salts, sulfites, lead salts, thallium salts, rhodium salts or complex salts thereof, or iridium salts or complex salts thereof in the process of formation or physical ripening, of silver halide grains.

The silver halide to be used in the present invention is prepared in the presence of an iridium salt or its complex salt in an amount of $1 \times 10^{-8}$ to $1 \times 10^{-5}$ mol per mol of silver. The silver halide to be used in the present invention may be silver haloiodide having a greater silver iodide content in the surface thereof than the average silver iodide content. The use of an emulsion containing such a silver haloiodide provides a higher sensitivity and a higher gradation (i.e., a higher gamma value).

The silver halide emulsion to be used in the present invention may or may not be subjected to chemical sensitization. As methods for chemical sensitization of silver halide emulsions there have been known sulfur sensitization process, reduction sensitization process and noble metal sensitization process. These chemical sensitization processes may be used singly or in combination.

A typical example of noble metal sensitization process is gold sensitization process using a gold compound, particularly a gold complex. The chemical sensitizing agent may comprise complexes of noble metals other than gold, such as platinum, palladium, or rhodium. Specific examples of such sensitizing agents are described in U.S. Pat. No. 2,448,060 and British Pat. No. 618,016. As sulfur sensitizing agents there may be used sulfur compounds contained in gelatin, or various sulfur compounds such as thiosulfates, thioureas, thiazoles and rhodanines.

An iridium salt or rhodium salt may be preferably used before the completion of physical ripening, particularly during the formation of grains, in the process of preparation of silver halide emulsion.

In the present invention, the silver halide emulsion layer may preferably contain two monodispersed emulsions having different average particle sizes as disclosed in JP-A-61-223734 and JP-A-62-90646 in the light of increase in the maximum density (Dmax). The monodispersed grains having smaller average grain size may be preferably subjected to chemical sensitization. The chemical sensitization may be most preferably effected by sulfur sensitization. A monodispersed emulsion having greater average particle size may be or may not be subjected to chemical sensitization. A monodispersed emulsion having greater average particle size is normally susceptible to black dot and, therefore, not subjected to chemical sensitization. However, if a monodispersed emulsion having greater average particle size is subjected to chemical sensitization, the chemical sensitization may be most preferably effected so lightly that the emulsion does not develop black pepper. That is, such a chemical sensitization can be accomplished by using shorter chemical sensitization time, a lower chemical sensitization temperature or a lower added amount of chemical sensitizers than chemical sensitization for a monodispersed emulsion having smaller average particle size. The difference in sensitivity between a monodispersed emulsion having greater average particle size and a monodispersed emulsion having smaller average particle size is not particularly limited. However, the difference is preferably in the range of from 0.1 to 1.0 and particularly preferably from 0.2 to 0.7 as calculated in terms of $\Delta \log E$. A monodispersed emulsion having greater average particle size preferably has a higher sensitivity than a monodispersed emulsion having smaller average particle size. The sensitivity of each emulsion can be determined when a light-sensitive material is obtained by incorporating a hydrazine derivative in the emulsion and then coating the emulsion on a support and processing with a developing solution having a pH of 10.5 to 12.3 containing 0.15 mol/liter or more of sulfinic acid ion. The average particle size of the small size monodispersed grains is 90% or less and preferably 80% or less of that of the large size monodispersed grains. The average particle size of the silver halide emulsion grains is preferably in the range of from 0.02 to 1.0 μm and particularly preferably from 0.1 to 0.5 μm within which the average particle size of the large size and small size monodispersed grains preferably fall.

In the present invention, when two or more emulsions having different sizes are used, the coated amount of silver in the small size monodispersed emulsion is generally from 40 to 90% by weight and particularly preferably from 50 to 80% by weight based on the total coated amount of silver.

In the present invention, monodispersed emulsions having different particle sizes may be incorporated in the same emulsion layer or separately in separate emulsion layers. When the emulsions are incorporated in separate emulsion layers, the large size emulsion is preferably incorporated in the upper layer and the small size emulsion is preferably incorporated in the lower layer.

The total coated amount of silver is preferably in the range of from 1 to 8 g/m².

The light-sensitive material to be used in the present invention may comprise sensitizing dyes (e.g., cyanine dyes and merocyanine dyes) such as those described in JP-A-55-52050 (pp. 45–53), for the purpose of increasing sensitivity. These sensitizing dyes may be used singly or in combination. Combinations of sensitizing dyes are often used particularly for the purpose of supersensitization. In combination with a sensitizing dye, a dye which has no spectral sensitizing effect itself or a substance which does not substantially absorb visible light but exhibits a supersensitizing effect may be incorporated in the emulsion. Useful sensitizing dyes, dye combinations exhibiting a supersensitizing effect and substances exhibiting a supersensitizing effect are described in *Research Disclosure*, No. 17643, Vol. 176 (December, 1978), IV-J, page 23.

The photographic emulsion to be used in the present invention may comprise various compounds for the purpose of inhibiting fog during the preparation, preservation or photographic processing of the light-sensitive material or stabilizing the photographic properties thereof. Examples of such compounds include many compounds known as fog inhibitors (i.e., antifoggants) or stabilizers, such as azoles (e.g., benzothiazolium salt, nitroindazoles, chlorobenzimidazoles, bromobenzimidazoles, mercaptothiazoles, mercaptobenzothiazoles, mercaptothiadiazoles, aminotriazoles, benzothiazoles, nitrobenzotriazoles); mercaptopyrimidines; mercaptotriazines, thioketo compounds (e.g., oxazolinethione); azaindenes [e.g., triazaindenes, tetraazaindenes (particularly 4-hydroxy-substituted (1,3,3a,7)tetraazaindenes), pentaazaindenes]; benzenethiosulfonic acid; benzenesulfinic acid; and benzenesulfonic amide. Preferred among these compounds are benzotriazoles such as 5-methylbenzotriazole and nitroindazoles such as 5-nitroindazole. These compounds may be incorporated in the processing solution.

As suitable development accelerators or nucleation infectious development accelerators there may be used compounds such as those disclosed in JP-A-53-77616, JP-A-54-37732, JP-A-53-137133, JP-A-60-140340 and JP-A60-14959 or various nitrogen- or sulfur-containing compounds.

The optimum amount of these accelerators is incorporated depends on the type of accelerator, but is normally in the range of from $1.0 \times 10^{-3}$ to 0.5 g/m² and preferably $5.0 \times 10^{-3}$ to 0.1 g/m².

In the present light-sensitive material, a desensitizer may be incorporated in the photographic emulsion layer or other hydrophilic colloidal layers.

The organic desensitizer to be used in the present invention is specified by the redox potential determined by its polarographic half wave potential, i.e., polarography such that the sum of the polarograph anodic potential and the polarograph cathodic potential is positive. The measurement of polarographic redox potential is described in, e.g., U.S. Pat. No. 3,501,307. The organic desensitizer may preferably contain at least one water-soluble group such as a sulfonic group, a carboxylic group or a sulfone group. These water-soluble groups may form salts with organic bases (e.g., ammonia, pyridine, triethylamine, piperidine and morpholine) or alkaline metals (e.g., sodium, potassium).

As suitable organic desensitizers there may be preferably used those represented by the formulae (III) to (V) as described in JP-A-63-133145 (pp. 55–72).

The present organic desensitizer may be preferably present in the silver halide emulsion layer in an amount of from $1.0 \times 10^{-8}$ to $1.0 \times 10^{-4}$ mol/m² and particularly preferably from $1.0 \times 10^{-7}$ to $1.0 \times 10^{-5}$ mol/m2.

The present emulsion layer or other hydrophilic colloidal layers may comprise water-soluble dyes as a filter dye or for the purpose of inhibiting irradiation, or for other various purposes. As such a filter dye there may be used a dye for reducing photographic sensitivity, preferably an ultraviolet absorber having a maximum spectral absorption in the inherent sensitivity region of silver halide or a dye with a substantial light absorption in the region of from 380 to 600 nm for improving the safety against safelight when the light-sensitive material is treated as a bright room-type light-sensitive material.

These dyes may be preferably incorporated and fixed in the emulsion layer or in the upper part of the silver halide emulsion layer, i.e., the light-insensitive hydrophilic colloidal layer farther than the silver halide emulsion layer with respect to the support, together with a mordant depending on the purpose of application.

The amount of these dyes to be incorporated depends on the molar absorption coefficient of ultraviolet absorber and is normally in the range of from $1 \times 10^{-2}$ to 1 g/m$^2$, and preferably 50 mg to 500 mg/m$^2$.

The above-described ultraviolet absorber may be incorporated in the coating solution in the form of a solution in a proper solvent such as water, alcohol (e.g., methanol, ethanol, propanol), acetone, methyl cellosolve or mixtures thereof.

As such an ultraviolet absorber there may be used an aryl-substituted benzotriazole compound, 4-thiazolidone compound, benzophenone compound, cinnamic ester compound, butadiene compound, benzoxazole compound or ultraviolet absorbing polymer.

Specific examples of such ultraviolet absorbers are described in U.S. Pat. Nos. 3,533,794, 3,314,794, 3,352,681, 3,705,805, 3,707,375, 4,045,229, 3,700,455 and 3,499,762, JP-A-46-2784 and West German Patent Publication No. 1,547,863.

Examples of filter dyes include oxonol dyes, hemioxonol dyes, styryl dyes, merocyanine dyes, cyanine dyes and azo dyes. In order to reduce residual color after development, a water-soluble dye or a dye decolorizable by an alkali or sulfinic ion may be preferably used.

Specific examples of such dyes which can be used in the present invention include pyrazoloneoxonol dyes such as those described in U.S. Pat. No. 2,274,782, diarylazo dyes such as those described in U.S. Pat. No. 2,956,879, styryl dyes or butadiene dyes such as those described in U.S. Pat. Nos. 3,423,207 and 3,384,487, merocyanine dyes such as those described in U.S. Pat. No. 2,527,583, merocyanine dyes or oxonol dyes such as those described in U.S. Pat. Nos. 3,486,897, 3,652,284 and 3,718,472, enaminohemioxonol dyes such as those described in U.S. Pat. No. 3,976,661, and dyes such as those described in British Pat. Nos. 584,609 and 1,177,429, JP-A-48-85130, JP-A-49-99620 and JP-A-49-114420 and U.S. Pat. Nos. 2,533,472, 3,148,187, 3,177,078, 3,247,127, 3,540,887, 3,575,704 and 3,653,905.

These dyes may be incorporated in the coating solution for the present light-insensitive hydrophilic colloidal layer in the form of a solution in a proper solvent such as water, alcohol (e.g., methanol, ethanol, propanol), acetone, methyl cellosolve or a mixture thereof. The amount of these dyes to be used is normally in the range of from $1 \times 10^{-3}$ to 1 g/m$^2$ and particularly preferably from $1 \times 10^{-3}$ to 0.5 g/m$^2$.

The present photographic light-sensitive material may comprise an inorganic or organic film hardener in the photographic emulsion layer or other hydrophilic colloidal layers. As such a film hardener there may be used chromium salts, aldehydes such as formaldehyde and glutaraldehyde, N-methylol compounds such as dimethylolurea, active vinyl compounds such as 1,3,5-triacryloyl-hexahydro-s-triazine and 1,3-vinyl-sulfonyl-2-propanol, active halogen compounds such as 2,4-dichloro-6-hydroxy-s-triazine, and mucohalogenic acids, or combinations thereof.

The photographic emulsion layer or other hydrophilic colloidal layers in the light-sensitive material prepared according to the present invention may comprise various surface active agents for various purposes, for example, as coating aids, as antistatic agents, for improvement of sliding properties, for improving emulsification and dispersion, for preventing adhesion, or for improving photographic properties such as acceleration of development, increase of contrast, and sensitization, or like purposes. As such surface active agents there may be particularly preferably used polyalkylene oxides having a molecular weight of 600 or more as described in JP-B-58-9412 (the term "JP-B" as used herein refers to an "examined Japanese patent publication"). As a surface active agent to be used as an antistatic agent there may be particularly preferably used a fluorine-containing surface active agent such as those described in U.S. Pat. No. 4,201,586 and JP-A-60-80849 and JP-A-59-74554.

The present photographic light-sensitive material may comprise a matting agent such as silica, magnesium oxide or polymethyl methacrylate in the photographic emulsion layer or other hydrophilic colloidal layers for the purpose of preventing adhesion.

The present photographic emulsion may comprise a dispersion of a water-insoluble or sparingly water-soluble synthetic polymer for the purpose of improving the dimensional stability. For example, a polymer comprising as monomer components alkyl (meth)acrylate, alkoxyacryl (meth)acrylate, and glycidyl (meth)acrylate, singly or in combination, or a combination thereof with acrylic acid or methacrylic acid, may be used.

The silver halide emulsion layer and other layers in the present photographic light-sensitive material may preferably comprise a compound containing an acid group. Examples of such a compound containing an acid group include polymers or copolymers containing as repeating units organic acids such as salicylic acid, acetic acid or ascorbic acid, or acid monomers such as acrylic acid, maleic acid or phthalic acid. For these compounds, JP-A-61-223834, JP-A-61-228437, JP-A-62-25745 and JP-A-62-55642 can be referenced. Particularly preferred as low molecular compounds among these compounds are ascorbic acids. Particularly preferred as high molecular compounds among these compounds are water-dispersible latexes of copolymers comprising acid monomers such as acrylic acid and crosslinking monomers containing two or more unsaturated groups such as divinyl benzene.

When the present silver halide light-sensitive material is used to obtain ultrahigh contrast and high sensitivity, it is not necessary to use a conventional infectious developing solution or a highly alkaline developing solution with a pH value of nearly 13 as described in U.S. Pat. No. 2,419,975. Rather, a stable developing solution may be used.

In particular, the present silver halide light-sensitive material may be processed with a developing solution containing 0.15 mol/liter or more of sulfinic ion as a preservative and having a pH value of from 10.5 to 12.3 and particularly preferably from 11.0 to 12.0, to provide negative images with sufficiently ultrahigh contrast.

The developing agent to be incorporated in the present developing solution is not particularly limited. In order to assist in obtaining an excellent halftone quality, the present developing agent may preferably contain dihydroxybenzenes, or optionally a combination of dihydroxybenzenes and 1-phenyl-3-pyrazolidones, or a combination of dihydroxybenzenes and p-aminophenols. The present developing agent may be preferably used in an amount of from 0.05 to 0.8 mol/liter. If a combination of dihydroxybenzenes and 1-phenyl-3-pyrazolidones or a combination of dihydroxybenzenes and p-aminophenols is used, the former may be preferably used in an amount of 0.05 to 0.5 mol/liter or the latter may be preferably used in an amount of 0.06 mol/liter or less.

Examples of sulfites to be used as preservatives in the present invention include sodium sulfite, potassium sulfite, lithium sulfite, ammonium sulfite, sodium bisulfite, potassium bisulfite, and formaldehyde sodium bisulfite. Such a sulfite may be preferably used in an amount of 0.4 mol/liter or more and particularly preferably 0.5 mol/liter or more.

The present developing solution may comprise as a silver stain inhibitor a compound such as those described in JP-A-56-24347. As a dissolution aid to be incorporated in the developing solution there may be used a compound such as those described in JP-A-61-267759. As a pH buffer to be incorporated in the developing solution there may be used a compound such as those described in JP-A-60-93433 or JP-A-62-186259.

As described above, the compound represented by formula (I) may be incorporated in a high contrast light-sensitive material in combination with a negative-type emulsion. Alternatively, the compound of formula (I) may be used in combination with an internal latent image-type silver halide emulsion. Embodiments of such an arrangement will be described hereafter. In this case, the compound of formula (I) may be preferably incorporated in an internal latent image-type silver halide emulsion layer. Alternatively, the compound of formula (I) may be incorporated in a hydrophilic colloidal layer adjacent to the internal latent image-type silver halide emulsion layer. Such a hydrophilic colloidal layer may be a layer having any function so long as it does not prevent a nucleating agent from diffusing into silver halide grains. Examples of such a hydrophilic colloidal layer include coloring material layer, interlayer, filter layer, protective layer and antihalation layer.

The amount of compound (I) to be incorporated in the layer is preferably such an amount that when the internal latent image-type emulsion is developed with a surface developing solution, sufficient maximum density (e.g., silver density of 1.0 or more) is provided. In particular, a suitable amount of compound (I) to be incorporated in the layer depends on the properties of silver halide emulsion used, the chemical structure of nucleating agent and the developing conditions and, therefore, varies widely. However, a useful value of the amount of compound (I) to be used in the layer is in the range of from about 0.005 to 500 mg and preferably from about 0.01 to about 100 mg, per mol of silver in the internal latent image-type silver halide emulsion. If compound (I) is incorporated in a hydrophilic colloidal layer adjacent to the emulsion layer, the same value as described above may be used based on the amount of silver contained in the same area of the internal latent image-type emulsion layer. The definition of such an internal latent image-type silver halide emulsion is described in JP-A-61-170733 (upper column on page 10) and British Pat. No. 2,089,057 (pp. 18–20).

Examples of suitable internal latent image-type emulsions which can be used in the present invention are described in JP-A-63-108336 (line 14 on page 28 to line 2 on page 31). Examples of suitable silver halide grains which can be used in the present invention are described in JP-A-63-108336 (line 3 on page 31 to line 11 on page 32).

In the present light-sensitive material, the internal latent image-type emulsion may be spectrally sensitized with a sensitizing dye to blue light, green light, red light or infrared light in a relatively long wavelength. As such a sensitizing dye there may be used a cyanine dye, a merocyanine dye, a complex cyanine dye, a complex merocyanine dye, a holopolar cyanine dye, a styryl dye, a hemicyanine dye, an oxonol dye or a hemioxonol dye. Examples of these sensitizing dyes include cyanine dyes or merocyanine dyes such as those described in JP-A-59-40638, JP-A-59-40636 and JP-A-59-38739.

The present light-sensitive material may include a dye-forming coupler as a coloring material. Alternatively, the present light-sensitive material may be developed with a developing solution containing such a dye-forming coupler.

Specific examples of these cyan, magenta and yellow couplers which can be used in the present invention are described in the patents cited in *Research Disclosure*, Nos. 17643 (December, 1978, VII-D) and 18717 (November, 1979).

Couplers which develop a dye having a proper diffusibility, colorless couplers, DIR couplers which undergo coupling reaction to release a development inhibitor, or couplers which undergo coupling reaction to release a development accelerator may be used in the present invention.

Typical examples of yellow couplers which may be used in the present invention include oil protect-type acylacetamide couplers.

In the present invention 2-equivalent yellow couplers may preferably used. Typical examples of such 2-equivalent yellow couplers include oxygen atom-releasing type yellow couplers and nitrogen atom-releasing type yellow couplers. α-Pivaloylacetanilide couplers provide excellent fastness of color-forming dye and particularly fastness to light. α-Benzoylacetanilide couplers can provide a high color density.

As a suitable magenta coupler for the present invention there may be used an oil protect-type indazolone or cyanoacetyl and preferably a 5-pyrazolone coupler or a pyrazoloazole coupler such as pyrazolotriazoles. As such a 5-pyrazolone coupler there may be preferably used a coupler which is substituted by an arylamino group or an acylamino group in the 3-position in the light of hue of color-forming dye or color density.

Particularly preferred examples of releasing groups for such a 2-equivalent 5-pyrazolone coupler include nitrogen atom-releasing groups such as those described in U.S. Pat. No. 4,310,619 and arylthio groups such as those described in U.S. Pat. No. 4,351,897. 5Pyrazolone couplers containing ballast groups such as those described in European patent 73,636, can provide high color density.

As suitable pyrazoloazole couplers there may be used pyrazolobenzimidazoles such as those described in U.S. Pat. No. 3,379,899 and preferably pyrazolo[5,1-c][1,2,4]triazoles such as those described in U.S. Pat. No. 3,725,067, pyrazolotetrazoles such as those described in *Research Disclosure*, No. 24220 (June, 1984) or pyrazolopyrazoles such as those described in *Research*

*Disclosure,* No. 24230 (June, 1984). Imidazo[1,2-b]pyrazoles such as those described in European Pat. No. 119,741 may be preferably used because of their small subsidiary absorption of yellow light by color-forming dye and excellent fastness of color-forming dye to light. Pyrazolo[1,5-b][1,2,4]triazoles such as those described in European Pat. No. 119,860 may particularly preferably be used in the present invention.

As a suitable cyan coupler for the present invention there may be used an oil protect-type naphthol or phenol coupler. Typical examples of such a coupler include naphthol couplers such as those described in U.S. Pat. No. 2,474,293. Preferred examples of such couplers include oxygen atom-releasing-type-equivalent naphthol couplers such as those described in U.S. Pat. Nos. 4,052,212, 4,146,396, 4,228,233 and 4,296,200. Specific examples of such a phenol coupler are described in U.S. Pat. Nos. 2,369,929, 2,801,171, 2,772,162 and 2,895,826. Cyan couplers which are fast to heat and moisture may be preferably used in the present invention. Typical examples of such cyan couplers include phenol cyan couplers containing an ethyl group or a higher group in the meta-position of a phenol nucleus, 2,5-diacylamino-substituted phenol couplers and phenol couplers containing a phenylureido group in the 2-position and an acylamino group in the 5-position such as those described in U.S. Pat. No. 3,772,002.

In order to eliminate undesirable absorption of short wavelength range by a dye produced from a magenta or cyan coupler, a color negative light-sensitive material for use in cameras may preferably comprise a colored coupler.

The graininess of the light-sensitive material can be improved by using a coupler which contains a color-forming dye having a proper diffusibility. Specific examples of such a dye-diffusible coupler are provided in U.S. Pat. No. 4,366,237 and British Pat. No. 2,125,570. Specific examples of yellow, magenta or cyan couplers having a proper diffusibility are described in European Pat. No. 96,470 and West German Patent Application (OLS) No. 3,234,533.

Dye-forming couplers and the above-described special couplers may form a dimer or higher polymer. Typical examples of polymerized dye-forming couplers are described in U.S. Pat. Nos. 3,451,820 and 4,080,211. Specific examples of polymerized magenta couplers are described in British Pat. No. 2,102,173 and U.S. Pat. No. 4,367,282.

In order to satisfy the properties required for light-sensitive materials, the various couplers may be incorporated in combination in the same light-sensitive layer or singly in two or more different light-sensitive layers.

The standard amount of color coupler to be used is in the range of from 0.001 to 1 mol per mol of light-sensitive silver halide. Preferably, yellow couplers are used in an amount of from 0.01 to 0.5 mol per mol of light-sensitive silver halide, magenta couplers are used in an amount of 0.003 to 0.3 mol per mol of light-sensitive silver halide, and cyan couplers are used in an amount of 0.002 to 0.3 mol per mol of light-sensitive silver halide.

In the present invention, a developing agent such as hydroxybenzenes (e.g., hydroquinones), aminophenols or 3-pyrazolidones may be incorporated in the light-sensitive material.

The photographic emulsion to be used in the present invention may be also used in combination with a dye-providing compound (coloring material) for color diffusion transfer process which releases a diffusible dye in correspondence to the development of silver halide in order to provide transferred images on the image-receiving layer after a proper development process. As such coloring materials there have been known many coloring materials. In particular, a coloring material which normally stays nondiffusible but undergoes redox reaction with an oxidation product of a developing agent (or electron transfer agent) to make cleavage, causing the release of a diffusible dye, may be preferably used (hereinafter to be referred to as "DRR compound"). Particularly preferred among these DRR compounds are DRR compounds containing N-substituted sulfamoyl groups. DRR compounds containing o-hydroxyarylsulfamoyl groups such as those described in U.S. Pat. Nos. 4,055,428, 4,053,312 and 4,336,322, or DRR compounds containing redox mother nucleus such as those described in JP-A-53-149328 may be preferably used in combination with the present nucleating agents. The combined use of such a DRR compound gives a rather small temperature dependence particularly during processing.

Specific examples of DRR compounds further include magenta dye-forming materials such as 1-hydroxy2-tetramethylenesulfamo-yl-4-[3,-methyl-4,-(2″-hydroxy-4″-methyl-5″-hexadecyloxyphenylsulfamoyl)-phenylazo]naphthalene.

The details of color couplers which can be preferably used in the present invention are provided in JP-A-53-149328 (line 18 on page 33 to end of page 40).

The present light-sensitive material, which has been imagewise exposed to light, may be preferably color developed with a surface developing solution having a pH value of 11.5 or less containing an aromatic primary amine color developing agent after or while being fogged with light or a nucleating agent, and then bleached and fixed to provide direct positive color images. The pH value of the developing solution may be preferably in the range of 10.0 to 11.0.

The fogging process may be effected in either a so-called "light fogging process" by which the entire surface of the light-sensitive layer is given a second exposure or a so-called "chemical fogging process" by which the light-sensitive material is developed in the presence of a nucleating agent. The present light-sensitive material may be developed in the presence of a nucleating agent and fogging light. Alternatively, a light-sensitive material containing a nucleating agent may be fogwise exposed to light.

The details of the light fogging process are provided in JP-A-63-108336 (line 4 on page 47 to line 5 on page 49). The details of nucleating agents which can be used in the present invention are provided in JP-A-63-108336 (line 6 on page 49 to line 2 on page 67). In particular, the compounds represented by formulae (N-1) and (N-2) may be preferably used in the present invention. Specific examples of these compounds include those represented by the formulae (N-I-1) to (N-I-10) described on pages 56 to 58 in the above Japanese patent application and those represented by the formulae (N-II-1) to (N-II-12) are described on pages 63 to 66 of that patent application.

Details of nucleation accelerating agents which can be used in the present invention are also provided in the above Japanese patent application (see line 11 on page 68 to line 3 on page 71). Particularly preferred among these nucleation accelerators are those represented by the formulae (A-1) to (A-13) described on pages 69 to 70 of the above patent application.

Details of color developing solutions which can be used in the development of the present light-sensitive material are provided on pages 71, line 4 to page 72, line 9 of the above Japanese patent application. Specific examples of aromatic primary amine color developing agents which can be preferably used in the present invention include p-phenylenediamine compounds. Typical examples of such p-phenylenediamine compounds include 3-methyl-4-amino-N-ethyl-N-($\beta$-methanesulfonamidoethyl)aniline, 3-methyl-4-amino-N-ethyl-N-($\beta$-hydroxyethyl)aniline, 3-methyl-4-amino-N-ethyl-N-methoxyethylaniline, and sulfates and hydrochlorides thereof.

When the present light-sensitive material is subjected to a color diffusion transfer processing to form direct positive color images thereon, there may be used a black-and-white developing agent such as a phenidone derivative, in addition to the above-described color developing agent.

A photographic emulsion layer which has been color developed is normally subjected to bleaching. The bleaching may be effected simultaneously with fixation (combined bleaching and fixing) or separately from fixation. In order to further expedite the processing, bleaching may be followed by blixing or fixation may be followed by blixing. The present bleaching solution or blixing solution may normally comprise an iron aminopolycarboxylate complex as the bleaching agent. As additives to be incorporated in the present bleaching solution or blixing solution there may be used various compounds such as those described in JP-A-62-215272 (pp. 22-30). The desilvering process (blixing or fixation) may be followed by rinse and/or stabilization. The rinsing solution or stabilizing solution may preferably comprise softened water. In the process for softening water, an ion exchange resin or reverse osmosis apparatus as described in JP-A-62-288838 may be used. Specific examples of such a water softening process which can be used in the present invention are described in JP-A-62-288838.

As additives to be incorporated in the rinsing solution or stabilizing solution there may be used various compounds such as those described in JP-A-62-215272 (pp. 30-36).

The less replenisher of each processing solution, the better is the resulting property. The replenished amount of each processing solution is preferably in the range of from 0.1 to 50 times and particularly preferably from 3 to 30 times the amount of the solution carried over by the light-sensitive material from the prebath per unit area.

In the interest of brevity and conciseness, the contents of the aforementioned numerous patents and articles are hereby incorporated by reference.

The present invention will be further described in the following Examples, but the present invention should not be construed as being limited thereto.

EXAMPLE 1

A multilayer color light-sensitive material Sample A was prepared by coating various layers of the undermentioned compositions on a polyethylene support laminated on both surfaces of paper support.
Layer E9: Protective Layer
Layer E8: Ultraviolet Absorbing Layer p0 Layer E7: Blue-Sensitive Emulsion Layer
Layer E6: Interlayer
Layer E5: Yellow Filter Layer
Layer E4: Interlayer
Layer E3: Green-Sensitive Emulsion Layer
Layer E2: Interlayer
Layer E1: Red-Sensitive Emulsion Layer
Support: Polyethylene Support
Layer B1: Back Layer
Layer B2: Protective Layer

Layer Constitution

The composition of the various layers will be described hereafter. The values of coated amount are represented in gram per $m^2$. However, the coated amount of nucleating agent is represented in mol per $m^2$. The coated amount of silver halide emulsion and colloidal silver is represented in gram per $m^2$ as calculated in terms of amount of silver. The coated amount of spectral sensitizing dye is represented in terms of mol per mol of silver halide incorporated in the same layer.

Support

The support is a polyethylene-laminated paper containing a white pigment ($TiO_2$) and a bluish dye (ultramarine) in polyethylene on layer E1 side.

Layer E1

| | |
|---|---|
| Silver Halide Emulsion A | 0.26 |
| Spectral Sensitizing Dye ExSS-1 | $1.0 \times 10^{-4}$ |
| Spectral Sensitizing Dye ExSS-2 | $6.1 \times 10^{-5}$ |
| Gelatin | 1.11 |
| Cyan Coupler ExCC-1 | 0.21 |
| Cyan Coupler ExCC-2 | 0.26 |
| Ultraviolet Absorber ExUV-1 | 0.17 |
| Solvent ExS-1 | 0.23 |
| Development Adjustor ExGC-1 | 0.02 |
| Stabilizer ExA-1 | 0.006 |
| Nucleation Accelerator ExZS-1 | $3.0 \times 10^{-4}$ |
| Nucleating Agent ExZK-1 | $1.4 \times 10^{-5}$ |

Layer E2

| | |
|---|---|
| Gelatin | 1.41 |
| Color Stain Inhibitor ExKB-1 | 0.09 |
| Solvent ExS-1 | 0.10 |
| Solvent ExS-2 | 0.10 |

Layer E3

| | |
|---|---|
| Silver Halide Emulsion A | 0.23 |
| Spectral Sensitizing Dye ExSS-3 | $3.0 \times 10^{-4}$ |
| Gelatin | 1.05 |
| Magenta Coupler ExMC-1 | 0.16 |
| Dye Stabilizer ExSA-1 | 0.20 |
| Solvent ExS-3 | 0.25 |
| Development Adjustor ExGC-1 | 0.02 |
| Stabilizer ExA-1 | 0.006 |
| Nucleation Accelerator ExZS-1 | $2.7 \times 10^{-4}$ |
| Nucleating Agent ExZK-1 | $2.0 \times 10^{-5}$ |

Layer E4

| | |
|---|---|
| Gelatin | 0.47 |
| Color Stain Inhibitor ExKB-1 | 0.03 |
| Solvent ExS-1 | 0.03 |

-continued

| | |
|---|---|
| Solvent ExS-2 | 0.03 |

Layer E5

| | |
|---|---|
| Colloidal Silver | 0.09 |
| Gelatin | 0.49 |
| Color Stain Inhibitor ExKB-1 | 0.03 |
| Solvent ExS-1 | 0.03 |
| Solvent ExS-2 | 0.03 |

Layer E6

Same as Layer E4

Layer E7

| | |
|---|---|
| Silver halide Emulsion A | 0.40 |
| Spectral Sensitizing Dye ExSS-4 | $4.2 \times 10^{-4}$ |
| Gelatin | 2.17 |
| Yellow Coupler ExYC-1 | 0.51 |
| Solvent ExS-2 | 0.20 |
| Solvent ExS-4 | 0.20 |
| Development Adjustor ExGC-1 | 0.06 |
| Stabilizer ExA-1 | 0.006 |
| Nucleation Accelerator ExZS-1 | $5.0 \times 10^{-4}$ |
| Nucleating Agent ExZK-1 | $2.0 \times 10^{-5}$ |

Layer E8

| | |
|---|---|
| Gelatin | 0.54 |
| Ultraviolet Absorber ExUV-2 | 0.21 |
| Solvent ExS-4 | 0.08 |

Layer E9

| | |
|---|---|
| Gelatin | 1.28 |
| Acryl-Modified Copolymer of Polyvinyl Alcohol (modification degree: 17%) | 0.17 |
| Liquid Paraffin | 0.03 |
| Polymethacrylic Acid Methyl Latex Grains (average particle diameter: 2.8 μm) | 0.05 |

Layer B1

| | |
|---|---|
| Gelatin | 8.70 |

Layer B2

Same as Layer E9

Besides the above-described compositions, Gelatin Hardener ExGK-1 (0.01 to 20 wt% per the gelatin) and a surface active agent were incorporated in each layer.

Silver Halide Emulsion A

An aqueous solution of potassium bromide and sodium chloride and an aqueous solution of silver nitrate were added at the same time to an aqueous solution of gelatin comprising 3,4-dimethyl-1,3-thiazoline-2-thione and lead acetate in amounts of 0.5 g and 0.3 g based on 1 mol of silver, respectively, with vigorous stirring at a temperature of 55° C. for about 5 minutes to obtain a monodispersed emulsion of silver bromochloride grains having an average particle diameter of about 0.2 μm (silver bromide content: 40 mol%). Sodium thiosulfate and chloroauric acid (tetrahydrate) were added to the emulsion in amounts of 35 mg and 20 mg based on 1 mol of silver, respectively. The emulsion was then heated to a temperature of 55° C. over 60 minutes and subjected to chemical sensitization.

The emulsion was further processed under the same precipitation conditions as described above with the silver bromochloride grains as cores over 40 minutes to provide grain growth. Eventually, a monodispersed emulsion of core/shell silver bromochloride grains having an average particle diameter of 0.4 μm was obtained. The coefficient of variation in particle size of the grains was about 10%.

Sodium thiosulfate and chloroauric acid (tetrahydrate) were added to the emulsion in amounts of 3 mg and 3.5 mg based on 1 mol of silver, respectively. The emulsion was then heated to a temperature of 60° C. over 50 minutes and subjected to chemical sensitization. As a result, an internal latent image-type Silver Halide Emulsion A was obtained.

Compounds Used in the Preparation of Sample

Cyan Coupler ExCC-1

Cyan Coupler ExCC-2

Magenta Coupler ExMC-1

Yellow Coupler ExYC-1

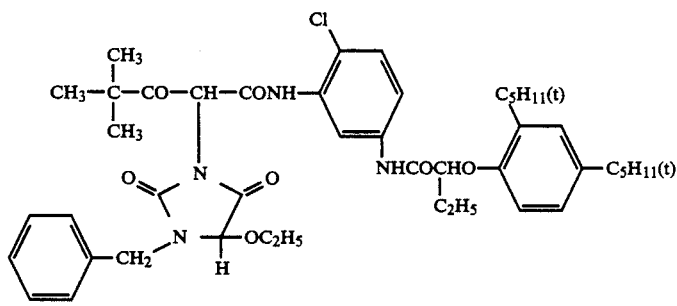
Spectral Sensitizing Dye ExSS-1
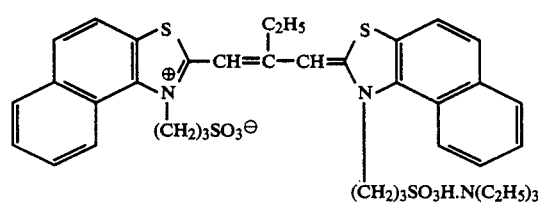
Spectral Sensitizing Dye ExSS-2
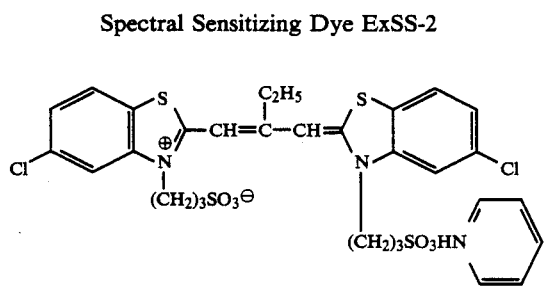
Spectral Sensitizing Dye ExSS-3
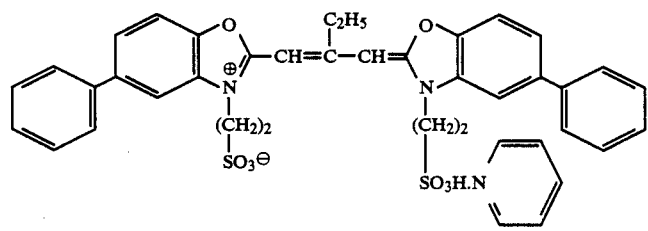
Spectral Sensitizing Dye ExSS-4
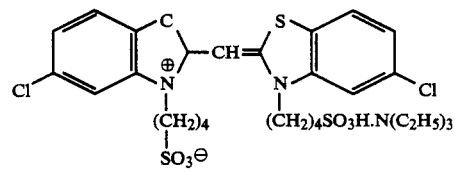
Solvent ExS-1
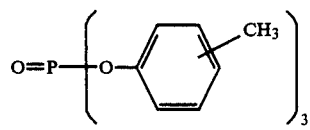
Solvent ExS-2
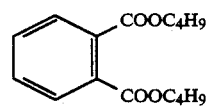
Solvent ExS-3
1/1 (volume ratio) mixture of:
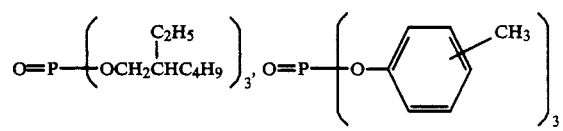
Solvent ExS-4
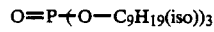
Ultraviolet Absorber ExUV-1
5/8/9 (weight ratio) of (1), (2) and (3):

Ultraviolet Absorber ExUV-2

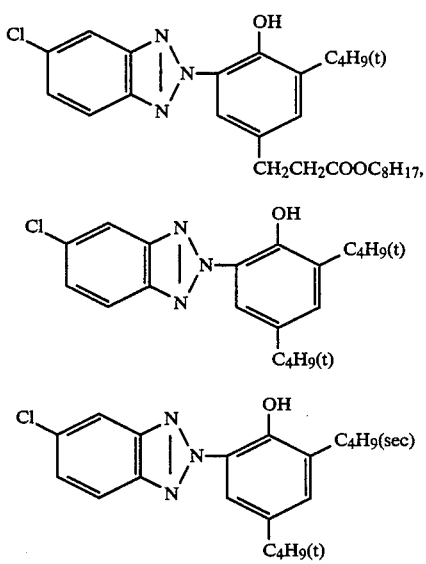

2/9/8 (weight ratio) mixture of (1), (2) and (3) as described above.

Dye Stabilizer ExSA-1

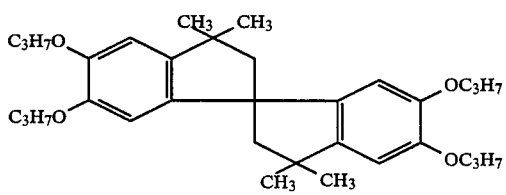

Color Stain Inhibitor ExKB-1

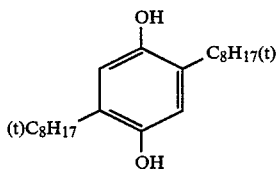

Development Adjustor ExGC-1

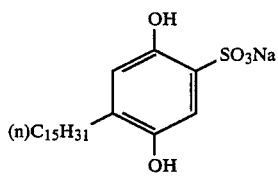

Stabilizer ExA-1

4-Hydroxy-5,6-trimethylene-1,3,3a,7-tetraazaindene

Nucleation Accelerator ExZS-1

2-(3-Dimethylaminopropylthio)-5-mercapto-1,3,4thiadiazole hydrochloride

Nucleating Agent ExZK-1

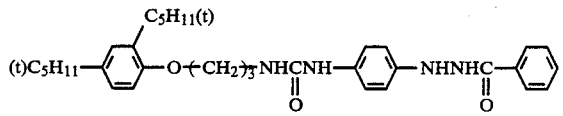

Nucleatinq Agent ExZK-2

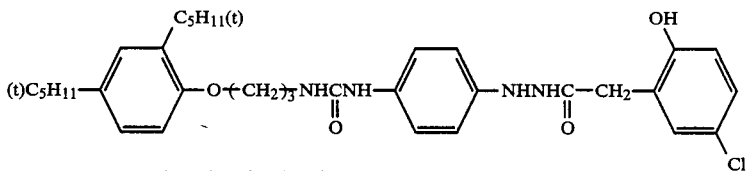

(described in JP-A-62-270948)

Gelatin Hardener ExGK-1

Sodium 1-oxy-3,5-dichloro-s-triazine

Processing Step A

| Step | Time (sec) | Temperature |
|---|---|---|
| Color Development | 100 | 38° C. |
| Blixing | 30 | " |
| Rinse 1 | 30 | " |
| Rinse 2 | 30 | " |

The replenishment of the rinsing solution was conducted in a countercurrent process in which the rinsing solution was replenished to the rinsing bath 2, and the overflow solution from the rinsing bath 2 was then passed to the rinsing bath 1.

Color Developing Solution

| | Mother Liquor (tank solution) |
|---|---|
| Diethylenetriaminepentaacetic Acid | 0.5 g |
| 1-Hydroxyethylidene-1,1-phosphonic Acid | 0.5 g |
| Diethylene Glycol | 8.0 g |
| Benzyl Alcohol | 10.0 g |
| Sodium Bromide | 0.5 g |
| Sodium Chloride | 0.7 g |
| Sodium Sulfite | 2.0 g |
| N,N-Diethylhydroxylamine | 3.5 g |

-continued

|  | Mother Liquor (tank solution) |
|---|---|
| 3-Methyl-4-amino-N-ethyl-N-($\beta$-methanesulfonamidoethyl)aniline | 6.0 g |
| Potassium Carbonate | 30.0 g |
| Fluorescent Brightening Agent (stilbene series) | 1.0 g |
| Pure Water to make | 1,000 ml |
| pH adjusted with potassium hydroxide or hydrochloric acid | 10.50 |

Blixing Solution

|  | Mother Liquor (tank solution) |
|---|---|
| Ammonium Thiosulfate | 110 g |
| Sodium Hydrogensulfite | 10 g |
| Ferric Ammonium Ethylenediaminetetraacetate (dihydrate) | 40 g |
| Disodium Ethylenediaminetetraacetate (dihydrate) | 5 g |
| 2-Mercapto-1,3,4-triazole | 0.5 g |
| Pure water to make | 1,000 ml |
| pH adjusted with aqueous ammonia or hydrochloric acid to | 7.0 |

Rinsing Solution

Pure water was used.

The pure water was obtained by subjecting tap water to an ion exchange process so that the concentration of all cations other than hydrogen ion and all anions other than hydroxyl ion was reduced to 1 ppm or less.

Multilayer color light-sensitive Material Nos. 1 to 10 were prepared in the same manner as in Sample A except that the nucleating agent (ExZK-1) was replaced by the compounds shown in Table 1.

The samples thus prepared were then wedgewise exposed to light (1/10 second, 10 CMS), subjected to Processing Step A, and measured for cyan color image density.

The results are shown in Table 1.

TABLE 1

| Sample No. | Nucleating Agent | Cyan Image Density | |
|---|---|---|---|
|  |  | Dmax | Dmin |
| 1 | Exemplary Compound 1 | 1.9 | 0.26 |
| 2 | Exemplary Compound 2 | 1.8 | 0.26 |
| 3 | Exemplary Compound 3 | 2.0 | 0.26 |
| 4 | Exemplary Compound 4 | 1.8 | 0.27 |
| 5 | Exemplary Compound 7 | 1.8 | 0.27 |
| 6 | Exemplary Compound 8 | 1.9 | 0.26 |
| 7 | Exemplary Compound 9 | 1.9 | 0.26 |
| 8 | Exemplary Compound 14 | 2.0 | 0.26 |
| 9 | Exemplary Compound 17 | 2.0 | 0.26 |
| 10 | Exemplary Compound 20 | 1.9 | 0.26 |
| A | ExZK-1 | 1.3 | 0.29 |
| B | ExZK-2 | 1.6 | 0.28 |

The added amount of nucleating agent was equivalent to that of ExZK-1. ExZK-1 and ExZK-2 are shown above.

Sample Nos. 1 to 10 comprising the present nucleating agents exhibited higher maximum image densities (Dmax) than Comparative Samples A and B. As to magenta density and yellow density, similar results were obtained.

EXAMPLE 2

Light-sensitive element Sample Nos. 1 to 8 were prepared by coating the following layers on a transparent polyethylene terephthalate support in the order described below.

(1) Mordant layer containing 3.0 g/m² of a copolymer containing the following repeating units in the following proportion as described in U.S. Pat. No. 3,898,088 and 3.0 g/m² of gelatin:

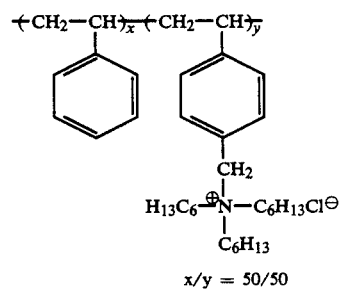

$x/y = 50/50$ (2) White reflective layer containing 20 g/m² of titanium oxide and 2.0 g/m² of gelatin (3) Light screening layer containing 2.70 g/m² of carbon black and 2.70 g/m² of gelatin (4) Layer containing 0.45 g/m² of the undermentioned magenta DRR compound, 0.10 g/m² of diethyllaurylamide, 0.0074 g/m² of 2,5-di-t-butylhydroquinone, and 0.76 g/m² of gelatin:

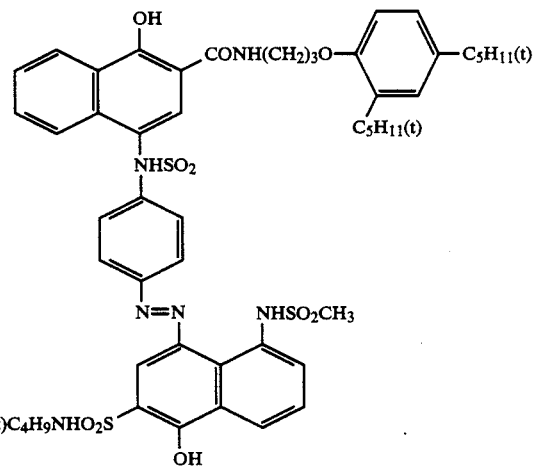

(5) Green-sensitive internal latent image-type direct positive silver bromoiodide emulsion layer (silver iodide content: 2 mol%) containing an internal latent image-type emulsion (1.4 g/m² as calculated in terms of amount of silver), a green-sensitive sensitizing dye (1.9 mg/m²) and a nucleating agent as shown in Table 2 and sodium 5-pentadecylhydroquinone-2-sulfonate (0.11 g/m²)

(6) Layer containing 0.94 g/m² of gelatin

The light-sensitive element Sample Nos. 1 to 8 were then combined with the following elements.

Processing Solution

| | |
|---|---|
| 1-Phenyl-4-methyl-4-hydroxymethyl-3-pyrazolidone | 10 g |
| Methyl Hydroquinone | 0.18 g |
| 5-Methylbenzotriazole | 4.0 g |
| Sodium Sulfite (anhydride) | 1.0 g |
| Sodium Carboxymethyl Cellulose Salt | 40.0 g |
| Carbon Black | 150 g |
| Potassium Hydroxide (28 wt % aq. soln.) | 200 ml |
| $H_2O$ | 550 ml |

The above-described processing solution was packed in the same pressure-rupturable vessels.

Cover Sheet

A cover sheet was prepared by coating 15 g/m² of polyacrylic acid (10 wt% aqueous solution having a viscosity of about 1,000 cp) as an acidic polymer layer (neutralizing layer) on a polyethylene terephthalate support and 3.8 g/m² of acetyl cellulose (hydrolysis of 100 g of acetyl cellulose produces 39.4 g of acetyl group) and 0.2 g/m² of a styrene-maleic anhydride copolymer having a composition (molar) proportion of styrene to maleic anhydride of about 60/40 and a molecular weight of about 50,000, as neutralization timing layer thereon.

Forced Deterioration Test

Two sets of the light-sensitive element Sample Nos. 1 to 8 were prepared. One of the sets was stored in a refrigerator at a temperature of 5° C., and the other was allowed to stand at a temperature of 35° C. and a relative humidity of 80% over 4 days.

Processing Step

The above-described cover sheet and the light-sensitive sheets thus obtained were laminated together. The light-sensitive sheets were then exposed to light from the cover sheet side through a color test chart. The above-described processing solution was then spread between the cover sheet and the light-sensitive sheets to a thickness of 75 μm by means of a pressure roller. The processing was effected at a temperature of 25° C. After processing, the light-sensitive sheets were processed using a Macbeth reflection densitometer. After 1 hour, the green density of images formed on the image-receiving layer was measured through the transparent support of the light-sensitive sheets. The results are shown in Table 2.

TABLE 2

| Light-Sensitive Element No. | Nucleating Agent Type | Added Amount (mg/m²) | $D^F$max | $S^F$ | $S^W$ |
|---|---|---|---|---|---|
| 1 (Comparison) | Comparative Compound A* | 1.0 | 1.72 | 100 | 100 |
| 2 (Comparison) | Comparative Compound B | " | 1.45 | 98 | 106 |
| 3 (Invention) | Compound 1 | " | 2.12 | 98 | 104 |
| 4 (Invention) | Compound 2 | " | 2.05 | 97 | 103 |
| 5 (Invention) | Compound 3 | " | 2.06 | 100 | 103 |
| 6 (Invention) | Compound 4 | " | 2.08 | 98 | 102 |
| 7 (Invention) | Compound 8 | " | 2.04 | 97 | 104 |
| 8 (Invention) | Compound 9 | " | 2.10 | 100 | 102 |

$D^F$max: Maximum density of positive image portion of sample stored in a refrigerator
$S^F$: Relative sensitivity of positive image portion having a density of 0.5 of sample stored in a refrigerator with $S^F$ of light-sensitive element 1 as 100
$S^W$: Relative sensitivity of positive image portion having a density of 0.5 of sample stored at 35° C. and 80% RH over 4 days with $S^F$ of light-sensitive element 1 as 100.

*Comparative Compound A

[Structure: t-butyl substituted phenyl-O-(CH₂)₃-NHCNH-phenyl-NHNHC-phenyl, with C=O groups]

Comparative Compound B (n)C₁₆H₃₃CNH-phenyl-NHNHC-phenyl-CH₂OH, with C=O groups

The results described above show that the light-sensitive element Sample Nos. 3 to 8 comprising the present nucleating agents can exhibit easily a higher Dmax than the light-sensitive element Sample Nos. 1 and 2 prepared according to the conventional method using the same added amount of nucleating agent. It is also shown that the light-sensitive element Sample Nos. 3 to 8 exhibit little practical problems as to the change in sensitivity after aging.

EXAMPLE 3

In order to exemplify the present invention, the following Emulsion X was prepared.

Emulsion X

An aqueous solution of silver nitrate and an aqueous solution of potassium bromide were added to an aqueous solution of gelatin (pH 5.5) of 75° C. containing 20 mg/liter of thioether(1,8-dihydroxy-3,6-dithiooctane) at the same time at a constant flow rate with vigorous stirring, while the silver electrode potential was maintained by octahedral grains, in such a manner that silver nitrate was added in an amount of 1/8 mol for 5 minutes. As a result, a monodispersed emulsion of spherical AgBr grains having an average particle diameter of about 0.14 μm was obtained. Sodium thiosulfate and chloroauric acid (tetrahydrate) were added to the emulsion in amounts of 20 mg and 20 mg per mol of silver halide, respectively, to adjust the pH value thereof to 7.5. The emulsion was then subjected to chemical sensitization at a temperature of 75° C. for 80 minutes with vigorous stirring to prepare a core emulsion. An aqueous solution of silver nitrate (containing ⅞ mol of silver nitrate) and an aqueous solution of potassium bromide were added to the core emulsion at the same time with vigorous stirring for 40 minutes while a silver electrode potential was maintained such that octahedral grains grew so that shells were grown on the cores. As a result, a monodispersed emulsion of octahedral core/shell type emulsion grains having an average particle diameter of about 0.3 μm was obtained. The emulsion was then washed with water and desalted. After being heated and dissolved, the emulsion was adjusted to pH 6.5. Sodium thiosulfate and chloroauric acid (tetrahydrate) were added to the emulsion in amounts of 5 mg and 5 mg per mol of silver halide, respectively. The emulsion was then subjected to ripening at a temperature of 75° C. over 60 minutes to chemically sensitize the surface of the shells. Eventually, an internal latent image-type monodispersed emulsion of core/shell octahedral grains (i.e., Emulsion X) was obtained. The particle size distribution of the emulsion was measured using an electron microscope. As a result, it was found that the average particle diameter was 0.30 μm and the coefficient of variation in particle diameter (average particle diameter ×100/standard deviation) was 10%.

A panchromatic sensitizing dye 3,3,-diethyl-9-methyl thiacarbocyanine was added to Emulsion X in an amount of 5 mg per mol of silver halide. Exemplary Compounds 1, 2, 3 and 9 and Comparative Compound A were added to the emulsion as nucleating agents in the amounts shown in Table 3. Compound C was added to the emulsion as a nucleation accelerator in an amount of $1 \times 10^{-3}$ mol per mol of silver halide. The emulsion was then coated on a polyethylene terephthalate support in an amount of 2.8 g/m² as calculated in terms of amount of silver. At the same time, a protective layer comprising gelatin and a film hardener was coated on the coated layer. As a result, a direct positive photographic light-sensitive material sensitive to light up to the red ray was prepared.

The light-sensitive material thus prepared was then exposed to light from a 1 kw tungsten lamp (color temperature: 2,854° K) sensitometer through a step wedge over 0.1 second. The light-sensitive material was then developed with a Kodak Proster Plus processing solution (pH of developing solution: 10.7) at a temperature of 38° C. over 18 seconds in an automatic developing apparatus (Kodak Proster I Processor). The light-sensitive material was then washed with water, fixed, washed with water, and dried in the same developing apparatus. These samples were then measured for maximum density (Dmax), minimum density (Dmin) and relative sensitivity of direct positive image. The results are shown in Table 3.

Comparative Compound A

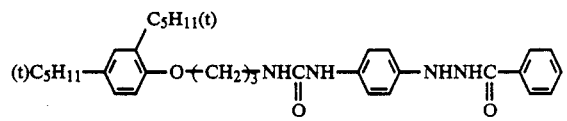

Compound C

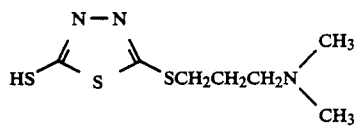

EXAMPLE 4

An aqueous solution of silver nitrate and an aqueous solution of potassium iodide and potassium bromide were simultaneously added to an aqueous solution of gelatin which had been kept at a temperature of 50° C. in the presence of iridium(III) potassium hexachloride in an amount of $4 \times 10^{-7}$ mol per mol of silver and ammonia for 60 minutes while the pAg value thereof was kept at 7.8. As a result, a monodispersed emulsion of cubic grains having an average particle diameter of 0.25 μm and an average silver iodide content of 1 mol% was obtained. The emulsion was not subjected to chemical sensitization. A sodium salt of 5,5,-dichloro-9-ethyl-3,3,-bis(3-sulfopropyl)oxacarbocyanine as a sensitizing dye, 4-hydroxy-6-methyl-1,3,3a,7-tetraazaindene as a stabilizer, a dispersion of polyethyl acrylate, polyethylene glycol, 1,3-vinylsulfonyl-2-propanol, and the compounds shown in Table 4 were added to these silver bromoiodide emulsions. The emulsions were each coated on a polyethylene terephthalate base in an

TABLE 3

| Sample No. | Nucleating Agent Type | Added Amount (mol/AgX mol) | Dmax | Dmin | Relative Sensitivity (D = 1.2) |
|---|---|---|---|---|---|
| 1 (Comparison) | Comparative Compound A | $1.0 \times 10^{-3}$ | 2.09 | 0.08 | 100 |
| 2 (Invention) | Exemplary Compound 1 | $1.0 \times 10^{-3}$ | 2.60 | 0.06 | 126 |
| | | $2.0 \times 10^{-3}$ | 2.71 | 0.07 | 118 |
| | | $3.0 \times 10^{-3}$ | 2.70 | 0.07 | 114 |
| 3 (Invention) | Exemplary Compound 2 | $1.0 \times 10^{-3}$ | 2.52 | 0.06 | 122 |
| | | $2.0 \times 10^{-3}$ | 2.63 | 0.07 | 109 |
| | | $3.0 \times 10^{-3}$ | 2.65 | 0.07 | 110 |
| 4 (Invention) | Exemplary Compound 3 | $1.0 \times 10^{-3}$ | 2.58 | 0.06 | 124 |
| | | $2.0 \times 10^{-3}$ | 2.65 | 0.07 | 112 |
| | | $3.0 \times 10^{-3}$ | 2.64 | 0.07 | 112 |
| 5 (Invention) | Exemplary Compound 9 | $1.0 \times 10^{-3}$ | 2.49 | 0.06 | 120 |
| | | $2.0 \times 10^{-3}$ | 2.52 | 0.07 | 114 |
| | | $3.0 \times 10^{-3}$ | 2.51 | 0.07 | 116 |

Table 3 shows the Exemplary Compounds 1, 2, 3 and 9 as nucleating agents exhibit higher reversal effects (i.e., reversal performance) and sensitivities than Comparative Compound A as control nucleating agent. That is, these novel nucleating agents exhibit an extremely high nucleation activity.

When these samples were developed with a developing solution whose pH value had been adjusted with an acid to 10.0, they had similarly higher reversal effects.

amount of 3.4 g/m² as calculated in terms of amount of silver. The coated amount of gelatin was 1.8 g/m².

A layer comprising 1.5 g/m² of gelatin, 0.3 g/m² of polymethyl methacrylate grains (average particle diameter: 2.5 μm) and the following surface active agents was coated on the emulsion coat as a protective layer.

Surface Active Agent

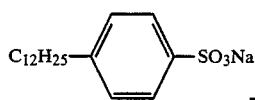
37 mg/m²

```
CH2COOC6H13
|
CHCOOC6H13          37 mg/m²
|
SO3Na

C8F17SO2NCH2COOK    2.5 mg/m²
       |
       C3H7
```

Comparative samples were prepared in the same manner as the aforementioned samples except that the compounds useful in the present invention were replaced by Comparative Compounds A, D, E and F. These compounds are shown in Table 4.

The samples were then exposed to light from a tungsten lamp (3,200° K) through an optical wedge, developed with the following developing solution at a temperature of 34° C. over 30 seconds, fixed, washed with water, and dried.

The resulting photographic properties are shown in Table 4.

Developing Solution I

| | |
|---|---|
| Hydroquinone | 50.0 g |
| N-Methyl-p-aminophenol | 0.3 g |
| Sodium Hydroxide | 18.0 g |
| Boric Acid | 54.0 g |
| Potassium Sulfite | 110.0 g |
| Disodium Ethylenediaminetetraacetate | 1.0 g |
| Potassium Bromide | 10.0 g |
| 5-Methylbenzotriazole | 0.4 g |
| 2-Mercaptobenzimidazole-5-sulfonic Acid | 0.3 g |
| Sodium 3-(5-Mercaptotetrazole)benzenesulfonate | 0.2 g |
| N-n-Butyldiethanolamine | 15.0 g |
| Sodium Toluenesulfonate | 8.0 g |
| Water to make | 1 liter |
| pH adjusted with potassium hydroxide to | 11.6 |

TABLE 4

| | | Nucleating Agent | | Photographic Properties | | | |
|---|---|---|---|---|---|---|---|
| Sample No. | | Compound | Added Amount (mol/mol-silver) | Sensitivity*1 | Gamma*2 | Halftone Quality*3 | Black Pepper*4 |
| 1 | Comparative Example-1 | — | 0 | Standard | 2.1 | 1 | 5 |
| 2 | Example-2 | Comparative Compound A | 2.1 × 10⁻³ | +0.53 | 14.0 | 4 | 5 |
| 3 | Example-3 | Compound D | " | +0.51 | 13.8 | 3 | 3 |
| 4 | Example-4 | Compound E | " | +0.55 | 14.4 | 3 | 3 |
| 5 | Example-5 | Compound F | " | +0.50 | 13.8 | 3 | 5 |
| 6 | Present Example-1 | Compound 1 | " | +0.78 | 18.2 | 5 | 5 |
| 7 | Example-2 | Compound 2 | " | +0.74 | 17.2 | 5 | 5 |
| 8 | Example-3 | Compound 3 | " | +0.77 | 17.6 | 5 | 5 |
| 9 | Example-4 | Compound 4 | " | +0.73 | 17.4 | 5 | 5 |
| 10 | Example-5 | Compound 9 | " | +0.71 | 17.0 | 5 | 5 |
| 11 | Example-6 | Compound 14 | " | +0.72 | 17.3 | 5 | 5 |
| 12 | Example-7 | Compound 17 | " | +0.76 | 18.0 | 5 | 5 |
| 13 | Example-8 | Compound 20 | " | +0.76 | 17.9 | 5 | 5 |

*1: The sensitivity is represented in terms of the difference from logE of the sensitivity of Comparative Example-1 as standard. Therefore, a sensitivity of +1.0 means a sensitivity 1.0 higher as calculated in terms of logE, e.g., 10 times higher than the blank.
*2: Gradation (γ): Gradation (γ) is represented in terms of gradient of the straight line from the point of dnesity of 3.0 to the point of density of 3.0 on the characteristic curve. The greater this value is, the harder the contrast.
*3: Halftone Quality: Hlaftone quality is visually evaluated if five grades. Evaluation "5" means "excellent", and evaluation "1" means "poorest". Halftone quality "5" and "4" are practical for halftone plate. Halftone quality "3" is poor but may be useful. Halftone quality "2" and "1" are impractical.
*4: Black Pepper: Black Pepper is evaluated in five grades under a microscope. Evaluation "5" means "excellent", and evaluation "1" means "poorest". Black pepper "5" and "4" are practical. Black pepper "3" is poor but may be useful. Black pepper "2" and "1" are inpractical.

Comparative Compound A

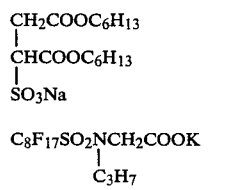

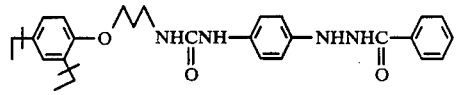

Comparative Compound D

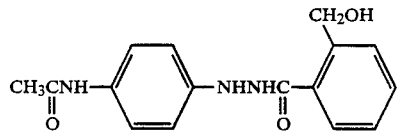

Comparative Compound E

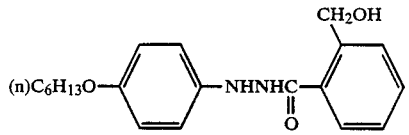

Comparative Compound F

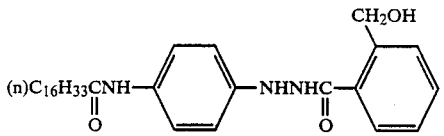

The above results show that the present compounds provide higher sensitivity and contrast when compared to the Comparative Compounds. It was also found that Comparative Compound F provides a better black pepper property than Comparative Compounds D and E but provides little improvement in γ and halftone quality while the present compounds provide higher contrast and improved halftone quality and black dot property.

EXAMPLE 5

The samples prepared in Example 4 were developed with the following developing solution at a temperature of 38° C. over 30 seconds, fixed, washed with water, and dried.

Developing Solution II

| | |
|---|---|
| Hydroquinone | 25 g |
| 4-Methyl-4-hydroxymethyl-1-phenyl-3-pyrazolidone | 0.5 g |
| Disodium Ethylenediaminetetraacetate | 10.8 g |
| Potassium Hydroxide | 10.5 g |
| Sodium Carbonate (monohydrate) | 11.0 g |
| Sodium Sulfite (anhydride) | 66.7 g |
| Potassium Bromide | 3.3 g |
| 5-Methylbenzotriazole | 0.4 g |
| Sodium 3-(5-Mercaptotetrazole)-benzenesulfonate | 0.2 g |
| Sodium 2-Mercaptobenzimidazole-5-sulfonate | 0.3 g |
| β-Phenethyl Alcohol | 2.0 ml |
| Water to make | 1 liter |
| pH adjusted with potassium hydroxide to | 10.7 |

The resulting photographic properties were shown in Table 5. With the present compounds, high sensitivity and contrast could be obtained from a developing solution having a low pH value of 10.7.

TABLE 5

| | Photographic Property | |
|---|---|---|
| Sample No. | Sensitvity | Gamma |
| 1 (Comparative Example-1) | Standard | 1.8 |
| 2 (Comparative Example-2) | +0.33 | 13.6 |
| 3 (Comparative Example-3) | +0.32 | 13.5 |
| 4 (Comparative Example-4) | +0.36 | 14.0 |
| 5 (Comparative Example-5) | +0.20 | 7.0 |
| 6 (Present Example-1) | +0.68 | 18.0 |
| 7 (Present Example-2) | +0.65 | 17.0 |
| 8 (Present Example-3) | +0.67 | 17.4 |

TABLE 5-continued

| | Photographic Property | |
|---|---|---|
| Sample No. | Sensitvity | Gamma |
| 9 (Present Example-4) | +0.63 | 17.2 |
| 10 (Present Example-5) | +0.60 | 16.8 |
| 11 (Present Example-6) | +0.62 | 17.1 |
| 12 (Present Example-7) | +0.67 | 17.8 |
| 13 (Present Example-8) | +0.66 | 17.7 |

EXAMPLE 6

An aqueous solution of silver nitrate and an aqueous solution of sodium chloride were simultaneously added to an aqueous solution of gelatin which had been maintained at a temperature of 40° C. in the presence of $(NH_4)_3RhCl_6$ in an amount of $5.0 \times 10^{-6}$ mol per mol of silver. Soluble salts were removed from the emulsion by a method (i.e., flocculation) commonly used in the art. Gelatin was then added to the emulsion. The emulsion was not subjected to chemical sensitization. 2-Methyl-4-hydroxy-1,3,3a,7-tetraazaindene was added to the emulsion as a stabilizer. As a result, a monodispersed emulsion of cubic grains having an average particle size of 0.18 μm was obtained.

Hydrazine compounds shown in Table 6 and polyethyl acrylate latexes were added to the emulsions in an amount of 30% by weight as calculated in terms of solid content. 1,3-Vinylsulfonyl-2-propanol was added to the emulsions as a film hardener. These emulsions were then each coated on a polyester support in an amount of 3.8 g/m² as calculated in terms of amount of silver. The coated amount of gelatin was 1.8 g/m² A layer comprising 1.5 g/m² of gelatin was coated on these emulsion coats as a protective layer.

The samples were then exposed to light through an optical wedge by a bright room printer ("P-607" manufactured by Dainippon Screen Co., Ltd.), developed with Developing Solution I used in Example 4 at a temperature of 38° C. over 20 seconds, fixed, washed with water, and dried.

The resulting photographic properties are shown in Table 6. Table 6 shows that the present compounds provide higher contrast and sensitivity than the Comparative Compounds.

TABLE 6

| | Nucleating Agent | | Photographic Property | |
|---|---|---|---|---|
| Sample No. | Compound | Added Amount (mol/mol silver) | Sensitivity | Gamma |
| 1 Comparative Example-1 | — | 0 | Standard | 7.0 |
| 2 Example-2 | Comparative Compound A* | $5.2 \times 10^{-3}$ | +0.32 | 11.8 |
| 3 Example-3 | Compound D | " | +0.23 | 11.5 |
| 4 Example-4 | Compound E | " | +0.34 | 12.0 |
| 5 Example-5 | Compound F | " | +0.15 | 7.5 |
| 6 Present Example-1 | Compound 1 | " | +0.66 | 14.7 |
| 7 Example-2 | Compound 2 | " | +0.59 | 13.8 |
| 8 Example-3 | Compound 3 | " | +0.65 | 14.2 |
| 9 Example-4 | Compound 4 | " | +0.60 | 13.7 |
| 10 Example-5 | Compound 9 | " | +0.55 | 13.5 |
| 11 Example-6 | Compound 14 | " | +0.60 | 13.8 |
| 12 Example-7 | Compound 17 | " | +0.64 | 14.8 |
| 13 Example-8 | Compound 20 | " | +0.63 | 14.5 |

*Comparative Compounds A, D, E and F are the same comparative compounds as used in Example 4.

EXAMPLE 7

Preparation of Emulsion

An aqueous solution of silver nitrate and an aqueous solution of sodium chloride containing ammonium hexachlorinated rhodiumate(III) in an amount of $0.5 \times 10^{-4}$ mol per mol of silver were mixed in a gelatin solution of 35° C. by a double jet process while the pH value thereof was adjusted to 6.5. As a result, a monodispersed emulsion of silver chloride grains having an average particle size of 0.07 μm was obtained.

Soluble salts were then removed from the emulsion by a flocculation method commonly known in the art. 4-Hydroxy-6-methyl-1,3,3a,7-tetraazaindene and 1-phenyl-5-mercaptotetrazole were added to the emulsion as stabilizers. The amount of gelatin and silver contained in 1 kg of the emulsion were 55 g and 105 g, respectively.

Preparation of Light-Sensitive Material

The present and comparative nucleating agents shown in Table 7 and the following nucleation accelerator and safelight dye were added to the emulsion thus obtained.

Nucleation Accelerator

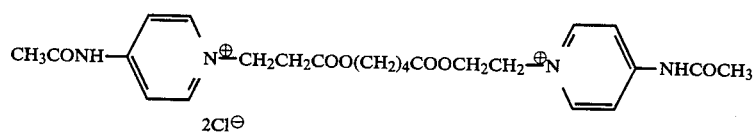

Added amount: 28.0 mg/m²

Safelight Dye

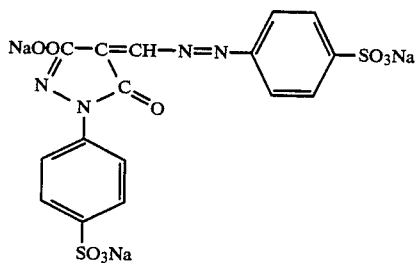

Added amount: 50.0 mg/m²

A polyethyl acrylate latex (14 mg/m²) and 2,4-dichloro-6-hydroxy-1,3,5-triazine sodium salt as a film hardener were added to the emulsion. The silver halide emulsion was then coated on a transparent polyethylene terephthalate support in an amount of 3.5 g per m² as calculated in terms of amount of silver. A protective layer comprising gelatin (1.3 g/m²), and the following three surface active agents, stabilizer and matting agent were coated on the emulsion coat and dried.

| | Added Amount (mg/m²) |
|---|---|
| Surface Active Agent | |
| $C_{12}H_{25}$—⟨phenyl⟩—$SO_3Na$ | 37 |
| $CH_2COOC_6H_{13}$<br>\|<br>$CHCOOC_6H_{13}$<br>\|<br>$SO_3Na$ | 37 |
| $C_8F_{17}SO_2NCH_2COOK$<br>\|<br>$C_3H_7$ | 2.5 |
| Stabilizer | |
| Thioctic Acid | 6.0 |
| Matting Agent | |
| Polymethyl Methacrylate (average particle diameter: 2.5 μm) | 9.0 |

These samples were then exposed to light through an optical wedge by a bright room printer ("P-607" manufactured by Dainippon Screen Co., Ltd.), developed with Developing Solution I at a temperature of 38° C. over 20 seconds, fixed, washed with water, and dried.

The resulting photographic properties are shown in Table 7.

The comparative examples provided a low gradation γ while the present copound provided high contrast images with a gradation γ of 10 or more. The comparative samples exhibited little or no increase in the sensitivity while the present samples exhibited a remarkable increase in the sensitivity.

TABLE 7

| Sample No. | Nucleating Agent Compound | Added Amount (mol/mol silver) | Photographic Property Sensitivity | Gamma |
|---|---|---|---|---|
| 1 Comparative Example-1 | — | 0 | Standard | 2.1 |
| 2 Example-2 | Comparative Compound A* | $6.4 \times 10^{-2}$ | +0.01 | 8.0 |
| 3 Example-3 | Compound D | " | +0.01 | 7.8 |
| 4 Example-4 | Compound E | " | +0.02 | 8.4 |
| 5 Example-5 | Compound F | " | ±0 | 5.2 |
| 6 Present Example-1 | Exemplary Compound 1 | " | +0.64 | 13.2 |
| 7 Example-2 | Compound 2 | " | +0.59 | 12.5 |
| 8 Example-3 | Compound 3 | " | +0.63 | 12.8 |
| 9 Example-4 | Compound 4 | " | +0.58 | 12.2 |
| 10 Example-5 | Compound 5 | " | +0.62 | 13.3 |

TABLE 7-continued

| Sample No. | Nucleating Agent | | Photographic Property | |
|---|---|---|---|---|
| | Compound | Added Amount (mol/mol silver) | Sensitivity | Gamma |
| 11 Example-6 | Compound 20 | " | +0.61 | 13.0 |

*Comparative Compounds A, D, E and F were the same as used in Example 4.

EXAMPLE 8

The present nucleating agents and comparative nucleating agents shown in Table 8 were added to the silver chloride emulsions such as those prepared in Example 6. 1-Phenyl-5-mercaptotetrazole (2.6 mg/m$^2$) and a polyethyl acrylate latex (30 wt% based on the amount of gelatin as calculated in terms of solid content) were added to the emulsions. 1,3-Vinylsulfonyl-2-propanol was added to these emulsions as film hardener in an amount of 2 wt% based on the amount of gelatin. The emulsions were each coated on a polyester support in an amount of 3.8 g/m2 as calculated in terms of amount of silver. The coated amount of gelatin was 1.8 g/m$^2$. The coating solutions had been prepared and coated under the following two conditions:

Condition 1

All the additives were rapidly added to the emulsion. The emulsions are immediately (within 1 hour) coated on the support.

Condition 2

A nucleating agent and 1-phenyl-5-mercaptotetrazole were added to the emulsion. The emulsion was then aged at a temperature of 40° C. over 24 hours. A polyethyl acrylate latex and 1,3-vinylsulfonyl-2-propanol were then added to the emulsion. The emulsion was immediately coated on the support.

A protective layer comprising gelatin (1.5 g/m$^2$), and the following three surface active agents, stabilizer and matting agent as coating aids were then coated on the emulsion coats.

Surface Active Agent

| | |
|---|---|
| $C_{12}H_{25}$—⌬—$SO_3Na$ | 37 mg/m$^2$ |
| $CH_2COOC_6H_{13}$<br>\|<br>$CHCOOC_6H_{13}$<br>\|<br>$SO_3Na$ | 37 mg/m$^2$ |
| $C_8F_{17}SO_2NCH_2COOK$<br>\|<br>$C_3H_7$ | 2.5 mg/m$^2$ |

Stabilizer
| | |
|---|---|
| Thioctic Acid | 2.1 mg/m$^2$ |

Matting Agent
| | |
|---|---|
| Polymethyl Methacrylate (average particle diameter: 2.5 μm) | 9.0 mg/m$^2$ |
| Silica (average particle diameter: 4.0 μm) | 9.0 mg/m$^2$ |

The samples were then evaluated for photographic properties in the same manner as in Example 6. The results are shown in Table 8. It can be seen that the sample representing the invention exhibited little change in photographic properties even when they included a coating solution which had been aged.

The coating solutions were examined for filterability under the test conditions shown in Table 8. The results are also shown in Table 8. After aging, the coating solutions comprising the comparative nucleating agents produced precipitates that clogged the filter, greatly prolonging filtration time. On the other hand, the coating solutions comprising the nucleating agents suitable for use with the present invention exhibited a slight increase in filtration time.

TABLE 8

| | | Nucleating Agent | | Filtration Time of Coating Solution (sec)* | | Photographic Property | | | | | |
|---|---|---|---|---|---|---|---|---|---|---|---|
| | | | | | | Fog | | ΔFog Condition 2 minus | Sensitivity (S) | | ΔS Condition 1 minus |
| Sample No. | | Type | Added Amount (mol/mol Ag) | Condition 1 | Condition 2 | Condition 1 | Condition 2 | Condition 1 | Condition 1 | Condition 2 | Condition 2 |
| 1 | Comparative Example-1 | Comparative Compound G | 4.7 × 10$^{-3}$ | 21 | NG** | 0.038 | 0.061 | 0.023 | Standard | −0.15 | +0.15 |
| 2 | Comparative Example-2 | Comparative Compound H | " | 25 | NG** | 0.039 | 0.063 | 0.024 | +0.01 | −0.17 | +0.16 |
| 3 | Present Example-1 | Compound 1 | " | 13 | 24 | 0.038 | 0.039 | 0.001 | +0.14 | +0.10 | +0.04 |
| 4 | Present Example-2 | Compound 2 | " | 12 | 21 | 0.039 | 0.041 | 0.002 | +0.13 | +0.10 | +0.03 |
| 5 | Present | Compound 4 | " | 15 | 23 | 0.039 | 0.042 | 0.003 | +0.15 | +0.12 | +0.03 |

TABLE 8-continued

| | | | Filtration Time of Coating Solution (sec)* | | Photographic Property | | | | | |
|---|---|---|---|---|---|---|---|---|---|---|
| | | | | | Fog | | ΔFog Condition 2 minus | Sensitivity (S) | | ΔS Condition 1 minus |
| Sample No. | Nucleating Agent Type | Added Amount (mol/mol Ag) | Condition 1 | Condition 2 | Condition 1 | Condition 2 | Condition 1 | Condition 1 | Condition 2 | Condition 2 |
| Example-3 | | | | | | | | | | |

Comparative Compound G

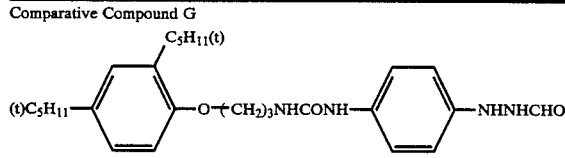

Comparative Compound H

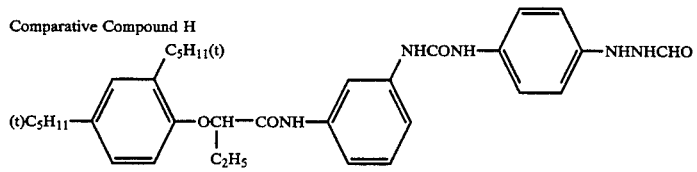

*Time required for 100 ml of coating solution to be filtered through a 1.2 cm diameter microfilter having an average pore diameter of 10 μm under the pressure of 1 pt/in²
**Clogged and unfilterable during filtration While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having thereon at least one of silver halide photographic emulsion layers and other hydrophilic colloidal layers, wherein said at least one of photographic emulsion layers and other hydrophilic colloidal layers contains a compound represented by formula (I)

$$X-N-N-G-R \quad (I)$$
$$\phantom{X-N}|\phantom{N}| $$
$$\phantom{X-N}A_1\ A_2$$

wherein at least one of $A_1$ and $A_2$ represents a hydrogen atom and the other represents a hydrogen atom, a sulfinic residual group or

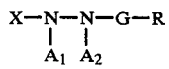

wherein $R_0$ represents an alkyl group, an alkenyl group, an aryl group, an alkoxy group or an aryloxy group, and $l_1$ represents an integer of 1 or 2; G represents

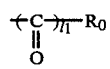

wherein $m_1$ represents an integer of 1 or 2, a sulfonyl group, a sulfoxy group,

wherein $R_1$ represents an alkoxy group or an aryloxy group, a thiocarbonyl group or an iminomethylene group; X represents an aliphatic group, an aromatic group or a heterocyclic group, substituted by the group represented by formula (a):

wherein Y represents a hydrogen atom, an aliphatic group, an aromatic group or a heterocyclic group; L represents

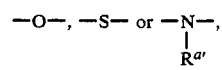

wherein $R_{a'}$ represents a hydrogen atom, an aliphatic group or an aromatic group; $R_a$ represents a hydrogen atom, an aliphatic group or an aromatic group; and R represents a group represented by formula (b):

wherein $R_b^1$ to $R_b^4$ may be the same or different and each represents a hydrogen atom, an aliphatic group or an aromatic group; B represents a suitable atomic group for forming 5- or 6-membered ring; Z represents a group capable of making a nucleophilic attack on G to separate the —G—R portion from the other portion of the formula; $m_b$ represents an integer of 0 or 1; $n_b$ represents an integer of 1 when Z is a hydroxy group, or $n_b$ represents an integer of 0 or 1 when Z represents a group other than a hydroxy group; and ($m_b+n_b$) represents an integer of 1 or 2.

2. The silver halide photographic material as claimed in claim 1, wherein the compound is contained in the silver halide photographic emulsion layer.

3. The silver halide photographic material as claimed in claim 1, wherein both $A_1$ and $A_2$ are hydrogen atoms.

4. The silver halide photographic material as claimed in claim 1 wherein G is the group

5. The silver halide photographic material as claimed in claim 1, wherein X is an aryl group.

6. The silver halide photographic material as claimed in claim 1, wherein L is —O—, l'S— or —NH—.

7. The silver halide photographic material as claimed in claim 1, wherein each of $R_b{}^1$, $R_b{}^2$, $R_b{}^3$ and $R_b{}^4$ in formula (b) is a hydrogen atom.

8. The silver halide photographic material as claimed in claim 1, wherein the substructure —G—R in formula (I) is represented by a group of formula (d):

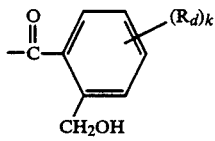

wherein $R_d$ is defined in the same manner as X, and k is 0, 1 or 2.

9. The silver halide photographic material as claimed in claim 8, wherein said compound represented by formula (I) is represented by formula (II):

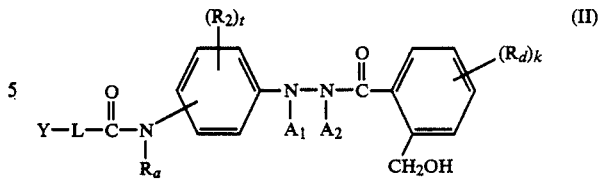

wherein at least one of $A_1$ and $A_2$ represents a hydrogen atom and the other represents a hydrogen atom, a sulfinic residual group or $$+C{\to}_{l_1}R_0$$
$$\phantom{+}\|$$
$$\phantom{+}O$$

wherein $R_0$ represents an alkyl group, an alkenyl group, an aryl group, an alkoxy group or an aryloxy group, and $l_1$ represents an integer or 2; L represents $$-O-,\ -S-\ \text{or}\ -N-,$$
$$\phantom{-O-,\ -S-\ \text{or}\ -}|$$
$$\phantom{-O-,\ -S-\ \text{or}\ -}R^{a\prime}$$

wherein $R_a{}'$ represents a hydrogen atom, an aliphatic group or an aromatic group; Y represents a hydrogen atom, an aliphatic group, an aromatic group or a heterocyclic group; $R_a$ represents a hydrogen atom, an aliphatic group or an aromatic group; $R_2$ represents a hydrogen atom, an aliphatic group, an aromatic group or a heterocyclic group; and t is 0, 1 or 2.

10. The silver halide photographic material as claimed in claim 1, wherein said compound represented by formula (I) is present in an amount ranging from about $1 \times 10^{-5}$ to about $5 \times 10^{-2}$ mol/mol of silver halide.

11. The silver halide photographic material as claimed in claim 10, wherein said compound represented by formula (I) is present in an amount ranging from about $2 \times 10^{-5}$ to about $1 \times 10^{-2}$ mol/mol of silver halide.

* * * * *